(12) United States Patent
Schütz et al.

(10) Patent No.: US 9,909,186 B2
(45) Date of Patent: Mar. 6, 2018

(54) PERSONALIZED BIOMARKERS FOR CANCER

(71) Applicant: Chronix Biomedical, San Jose, CA (US)

(72) Inventors: Ekkehard Schütz, Gottingen (DE); Julia Beck, Gottingen (DE); Howard Urnovitz, San Jose, CA (US)

(73) Assignee: Chronix Biomedical, San Jose, CA (US)

( * ) Notice: Subject to any disclaimer, the term of this patent is extended or adjusted under 35 U.S.C. 154(b) by 0 days.

(21) Appl. No.: 14/652,098

(22) PCT Filed: Dec. 13, 2013

(86) PCT No.: PCT/US2013/075015
§ 371 (c)(1),
(2) Date: Jun. 12, 2015

(87) PCT Pub. No.: WO2014/093825
PCT Pub. Date: Jun. 19, 2014

(65) Prior Publication Data
US 2016/0053328 A1  Feb. 25, 2016

Related U.S. Application Data

(60) Provisional application No. 61/737,626, filed on Dec. 14, 2012.

(51) Int. Cl.
*C12Q 1/68* (2006.01)

(52) U.S. Cl.
CPC ......... *C12Q 1/6886* (2013.01); *C12Q 1/6809* (2013.01); *C12Q 2600/106* (2013.01); *C12Q 2600/112* (2013.01); *C12Q 2600/156* (2013.01); *C12Q 2600/158* (2013.01)

(58) Field of Classification Search
CPC .............................. C12Q 1/6886; C12Q 1/6809
USPC ........................................................... 506/7
See application file for complete search history.

(56) References Cited

U.S. PATENT DOCUMENTS

| | | | |
|---|---|---|---|
| 5,773,649 A | 6/1998 | Sinnett et al. | |
| 6,344,317 B2* | 2/2002 | Urnovitz ............. | C12Q 1/6876 435/6.12 |
| 2004/0181048 A1 | 9/2004 | Wang | |
| 2007/0231823 A1* | 10/2007 | McKernan ........... | C12Q 1/6837 435/6.11 |
| 2012/0115744 A1* | 5/2012 | Raymond ............ | C12Q 1/6811 506/9 |
| 2012/0238463 A1 | 9/2012 | Goel et al. | |
| 2015/0275308 A1* | 10/2015 | Carlton ................ | C12Q 1/6881 435/6.11 |

FOREIGN PATENT DOCUMENTS

| | | |
|---|---|---|
| WO | 2012/037882 A1 | 3/2012 |
| WO | 2012/140224 A1 | 10/2012 |

OTHER PUBLICATIONS

Buck et al. (Biotechniques, 1999, 27(3), pp. 528-536).*
Lowe et al. (Nucleic Acids Research, 1990, 18(7), pp. 1757-1761).*
Rozen et al. (Methods in Molecular Biology, Bioinformatics and Protocols, 2000, pp. 365-386).*
Nolan et al. (Nature Protocols, Nov. 9, 2006, 1(3), pp. 1559-1582).*
Liggett et al. (Int J Cancer, Jan. 15, 2011, 128(2), pp. 492-499).*
Hoque et al. (Journal of Clinical Oncology, Sep. 6, 2006, 44(26), pp. 4262-4269).*
Aparicio et al., "LINE-1 Methylation in Plasma DNA As a Biomarker of Activity of DNA Methylation Inhibitors in Patients With Solid Tumors," *Epigenetics*, 4(3):176-184 (Apr. 2009).
Gosden, J., "Oligonucleotide Primed In Situ DNA Synthesis (PRINS)". In: *Methods in Molecular Biology*, vol. 29, Ch. 18, pp. 323-333: Chromosome Analysis Protocols. Edited by J.R. Gosden. Totowa, NJ, A Humana Press Inc., 1994.
Kitkumthorn et al., "LINE-1 and Alu Methylation Patterns in Lymph Node Metastases Head and Neck Cancers," *Asian Pacific Journal of Cancer Prevention*, 13(9):4469-4475 (Sep. 2012).
Xing et al., "Mobile Elements Create Structural Variation: Analysis of a Complete Human Genome," *Genome Research*, 19(9): 1516-1526 (May 2009).
International Search Report and Written Opinion from PCT/US2013/075015, dated Apr. 24, 2015.
Campbell et al., "Identification of somatically acquired rearrangements in cancer using genome-wide massively parallel paired-end sequencing," *Nature Genetics, Nature Publishing Group*, 40(6): 722-729 (Jun. 2008).
Kozeretska et al., "Mobile Genetic Elements and Cancer. From Mutations to Gene Therapy," *Experimental Oncology*, 33(4): 198-205 ( Dec. 2011).
Sunami et al., "Quantification of LINE1 in Circulating DNA as a Molecular Biomarker of Breast Cancer," *Annals of the New York Academy of Sciences, New York Academy of Sciences*, 1137: 171-174 (2008).

(Continued)

*Primary Examiner* — Karla A Dines
(74) *Attorney, Agent, or Firm* — Kilpatrick Townsend & Stockton LLP

(57) ABSTRACT

The invention provides methods and reagents for identifying personalized tumor biomarkers for a patient that has a solid tumor and methods of using such biomarkers to monitor patient responses to therapeutic treatments.

19 Claims, 24 Drawing Sheets

(56) References Cited

OTHER PUBLICATIONS

Zhang et al., "Alu distribution and mutation types of cancer genes," *BMC Genomics, Biomed Central Ltd.*, 12(1):157 (Mar. 2011).
Extended European Search Report from European Patent Application No. 13863107.2, dated Jun. 17, 2016.

\* cited by examiner

PERSONALIZED BIOMARKERS FOR CANCER

CROSS-REFERENCE TO RELATED APPLICATIONS

This application is the U.S. national stage entry of International Application No. PCT/US2013/075015, filed Dec. 13, 2013, which claims priority benefit of U.S. provisional application No. 61/737,626, filed Dec. 14, 2012, each of which is herein incorporated by reference for all purposes in their entireties.

REFERENCE TO SUBMISSION OF A SEQUENCE LISTING

This application includes a Sequence Listing as a text file named "083443-0947257-SUBSEQ_ST25.txt" created Sep. 17, 2015, and containing 8,277 bytes. The material contained in this text file is incorporated by reference in its entirety for all purposes.

BACKGROUND OF THE INVENTION

There is a need for methods to monitor the response of a cancer patient to a therapy. This invention addresses that need.

BRIEF SUMMARY OF THE INVENTION

The invention is based, in part, on the discovery that insertions of repetitive elements occur in tumors of cancer patients and that such an insertion region can be used as an individualized biomarker the particular patient to monitor the response of the patient to a therapy.

The invention provides methods of selecting a personalized biomarker for a patient having a tumor. The methods of the invention comprise (a) obtaining nucleic acid samples comprising DNA from the patient from each of the following sources: peripheral blood mononuclear cells (PBMCs) or other non-cancerous somatic cell sources like hair or buccal swap, the tumor, and pre-therapy cell-free nucleic acids, which nucleic acids are obtained prior to a therapy; (b) preparing a library of DNA fragments from each of the nucleic acid samples; (c) sequencing the DNA fragments in the libraries to identify DNA fragments that comprise a repetitive element insertion region; and (d) comparing repetitive element insertion regions identified in the PBMC or other non-cancerous somatic cell sources like hair or buccal swap sample to the repetitive element insertion regions identified in the tumor sample and/or the cell free nucleic acids sample to identify repetitive element insertion regions that are present in the tumor, but not PBMCs, thereby identifying a personalized biomarker for the patient. The biomarker can be any repetitive element, such as an Alu sequence, a short interspersed nuclear element (SINE), a long interspersed nuclear element (LINE), or an endogenous retroviruses (ERV).

In some embodiments, step (d) will further comprise comparing repetitive element insertion regions identified in the PBMC sample to the corresponding regions in the human genome database to identify insertion regions in the PBMC sample that are not present in the human genome database.

In a typical embodiment, the DNA from one or more of the samples will be amplified (e.g., using PCR). In this case, the methods may further comprise the steps of adding adapter sequences comprising universal priming sites to each of the DNA fragments and amplifying the DNA fragments, prior to sequencing the fragments. The PCR amplification can be carried out using a primer specific to the repetitive element and a universal primer, in which case only fragments comprising the repetitive element will be amplified. Thus, allowing for the identification of fragments comprising repetitive element insertions. Alternatively, step of amplifying can be carried out using two universal primers, in which case all fragments are amplified. Fragments comprising repetitive element insertions can also be identified and/or enriched using oligonucleotide probes specific for the repetitive element. The probes can be used to physically remove the desired DNA fragments comprising the repetitive element from other DNA fragments in the library, thereby enriching for the desired DNA fragments. The enrichment step can include, for example, attaching hybridization complexes comprising biotinylated probes to a solid support (e.g., a magnetic bead).

In some embodiments, the methods can further comprise the step of obtaining a nucleic acid sample from the patient from cell-free nucleic acids post-therapy, which nucleic acids are obtained following the therapy. In these embodiments, repetitive element regions identified the pre-therapy cell-free nucleic acid sample are compared to the post-therapy cell-free nucleic acid sample to identify repetitive element insertion regions that are not detected or greatly reduced in the post-therapy cell-free nucleic acid sample.

In one aspect, the invention provides a method of selecting a personalized biomarker for a patient having a tumor, the method comprising: (a) obtaining nucleic acid samples comprising DNA from the patient from each of the following sources: peripheral blood mononuclear cells (PBMCs), the tumor, pre-therapy cell-free nucleic acids, which nucleic acids are obtained prior to a therapy, and cell-free nucleic acids post-therapy, which nucleic acids are obtained following the therapy; (b) performing at least one amplification reaction on DNA from each of the nucleic acid samples using a primer to a repetitive element (e.g., an Alu sequence) and a universal primer; (c) sequencing the DNA obtained from the amplification reactions to determine regions that comprise the repetitive element insertion (e.g., an Alu insertion sequence) relative to the corresponding regions in the human genome database; (d) comparing insertion regions identified in step (c) from the PBMC sample to the insertion regions identified in step (c) from the tumor sample to identify insertion regions that are present in the tumor, but not PBMCs; (e) comparing the insertion regions identified in step (d) to the insertion regions identified in the cell-free nucleic acid sample from the patient pre-therapy to identify insertion regions that are present in the tumor sample and in the pre-therapy cell-free nucleic acid sample; and (f) comparing the tumor regions identified in step (e) to the insertion regions identified in the cell-free nucleic acid sample from the patient post-therapy to identify insertion regions that are not detected in the cell-free nucleic acid sample post-therapy, thereby identifying a personalized biomarker for the patient. In some embodiments of the methods of the invention, the therapy is surgery. In some embodiments, the therapy is radiation. In some embodiments, the therapy is chemotherapy In another aspect, the invention provides a method of selecting a personalized biomarker for a patient having a tumor, the method comprising: (a) obtaining a nucleic acid sample comprising DNA from circulating nucleic acids pre-therapy and a nucleic acid sample comprising DNA from the circulating nucleic acids post-therapy; (b) performing at least one amplification reaction on DNA from each of the nucleic acid samples using a primer to an sequence and a universal primer; (c) sequencing the DNA obtained from the amplification reactions to determine regions that comprise an insertion sequence relative to a normal human genome and can be uniquely positioned to a defined region in a normal human genome; (d) quantifying the level of an insertion region identified in step (c) from the pre-therapy circulating DNA sample in comparison to the level of the insertion regions present in normal controls to identify insertions regions that are present in circulating cell-free DNA at higher levels than normal controls; and (e) comparing the level of the insertion regions identified in step (d) to the level of the insertion regions in the post-therapy cell-free DNA sample to identify insertion regions that are not detected at a level different from normal, thereby identifying a personalized biomarker for the patient. In some embodiments of the methods of the invention, the therapy is surgery. In some embodiments, the therapy is radiation. In some embodiments, the therapy is chemotherapy In some embodiments of the methods of the invention, the method further comprises performing an additional amplification reaction on DNA from each of the nucleic acid samples wherein the second amplification reactions comprising a second primer to an Alu sequence and a second universal primer. In some embodiments, one of the amplification reactions comprises a primer pair comprising SEQ ID NO:5 and a universal primer; or a primer pair comprising SEQ ID NO:6 and a universal primer. In some embodiments, one of the amplification reactions comprises a primer pair comprising SEQ ID NO:5 and a universal primer and the additional amplification reactions comprises a primer pair comprising SEQ ID NO:6 and a universal primer.

Personalized biomarkers can be detected for a patient with any type of cancer. In some embodiments, the patient has breast cancer, colorectal cancer, prostate cancer, lung cancer, liver cancer, pancreatic cancer, ovarian cancer, cervical cancer, gastric cancer, squamous cell cancer of the head and neck, bladder cancer, or renal cancer. In some embodiments, the patient has a sarcoma. In some embodiments, the patient has a lymphoma or leukemia. In some embodiments, the patient has a solid tumor. In some embodiments, the patient has a breast tumor.

In a further aspect, the invention provides a method of monitoring the response of a patient that has a tumor to a therapy, the method comprising evaluating the level of an individualized biomarker obtained in accordance with any one of the preceding claims in cell-free circulating nucleic acids obtained from the patient before and after the therapy. In some embodiments, the therapy is surgery. In some embodiments, the therapy is radiation. In some embodiments, the therapy is chemotherapy.

DETAILED DESCRIPTION OF THE INVENTION

Figure 1:
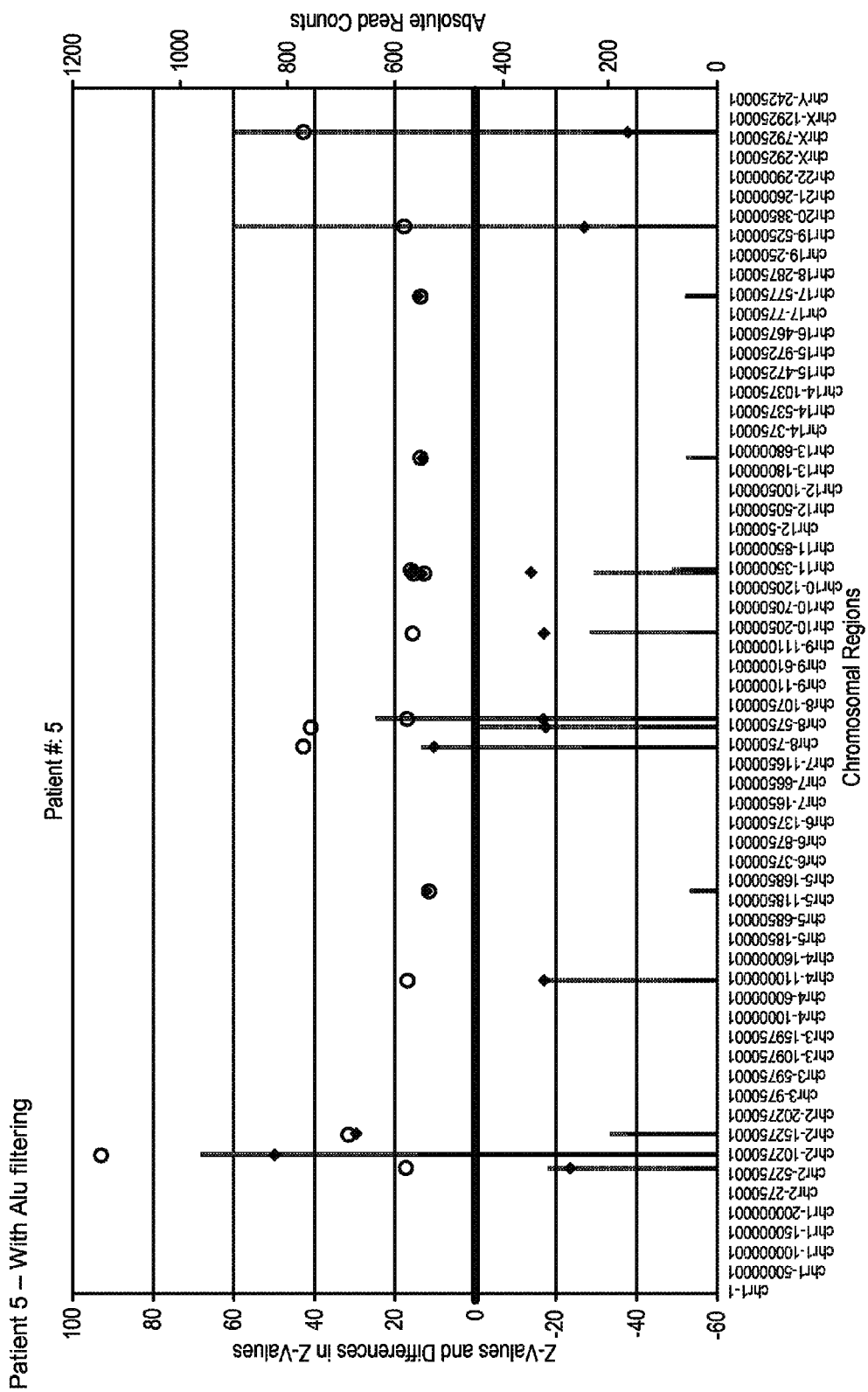
FIG. 1 shows a diagram illustrating cell-free DNA genomic region evaluation. Z-values pre-surgery (open circles) and differences in pre-surgery and post-surgery Z-values (filled diamonds) are shown. The bars represent the sums of reads per bin that went into the analyses. Bins where the pre-surgery Z-values <3 were censored to zero.
Figure 1:
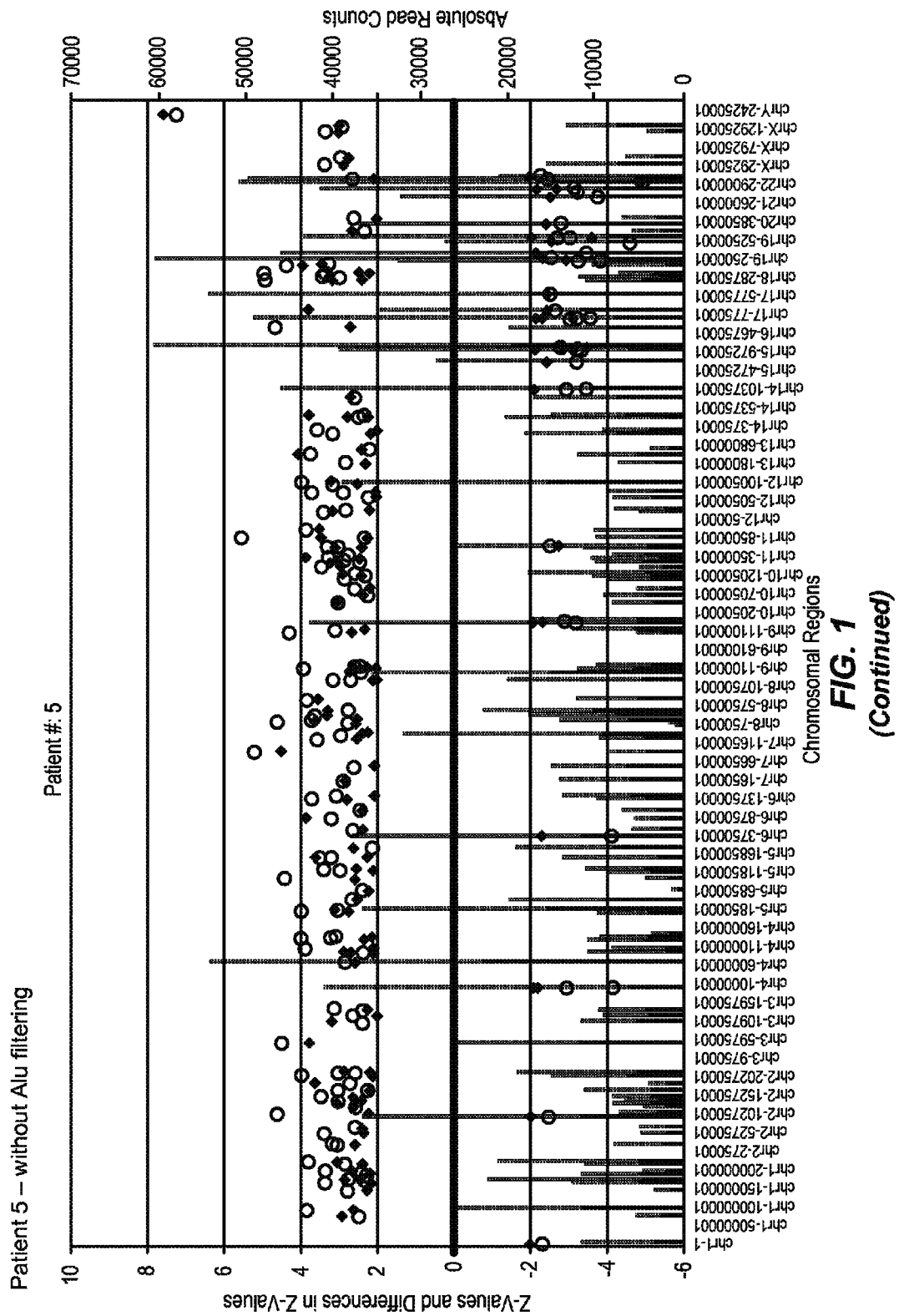
Figure 1:
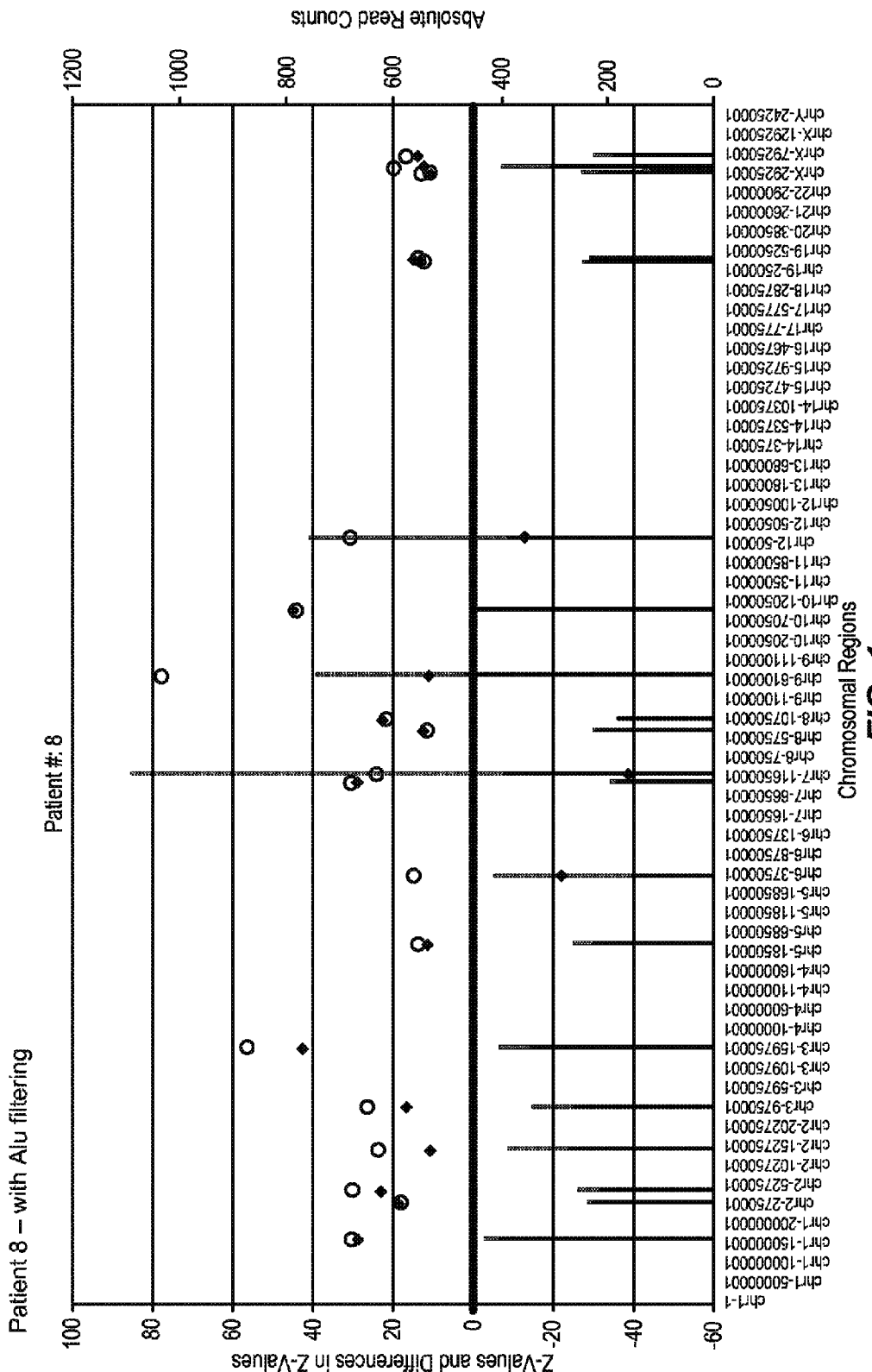
Figure 1:
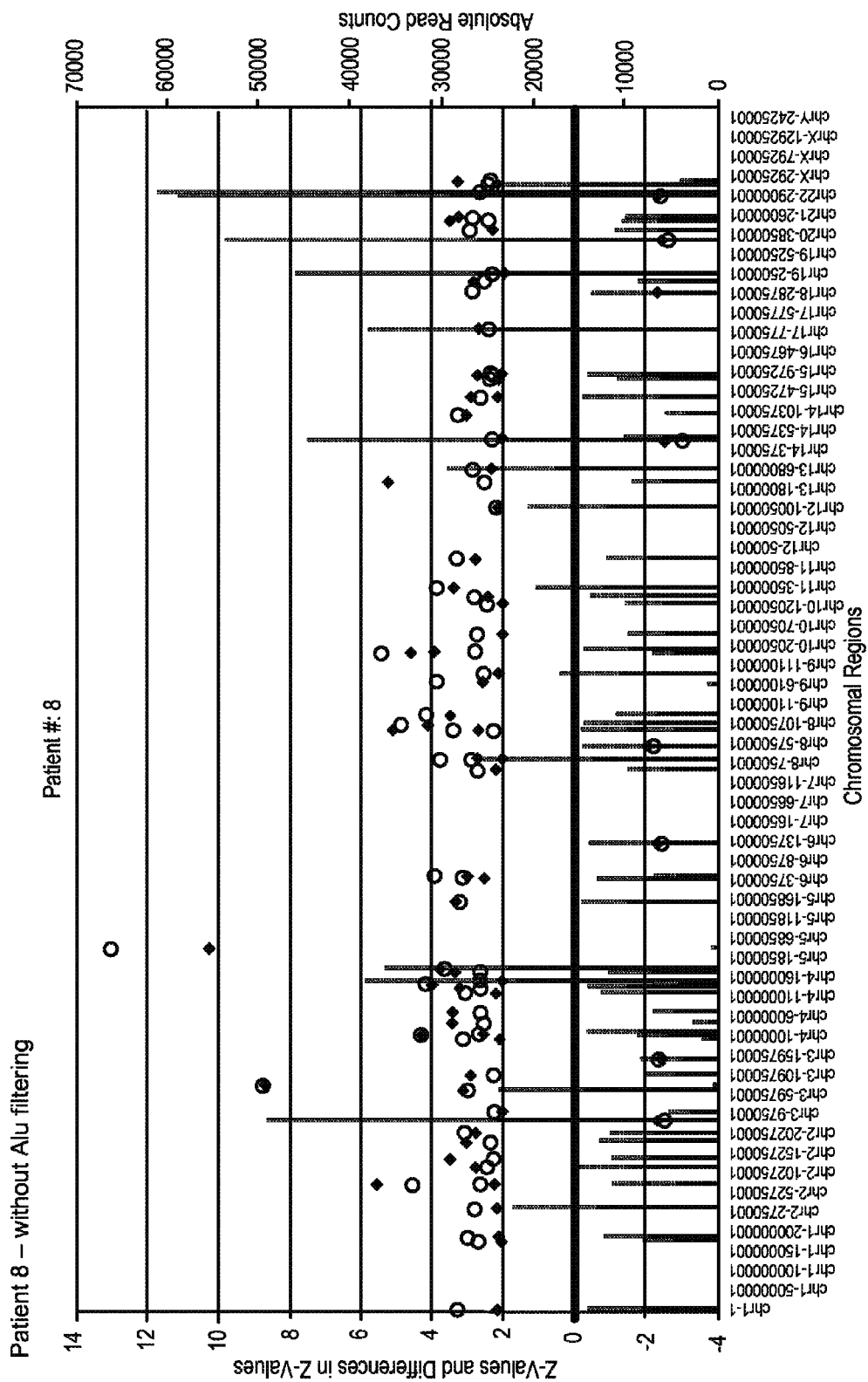
Figure 1:
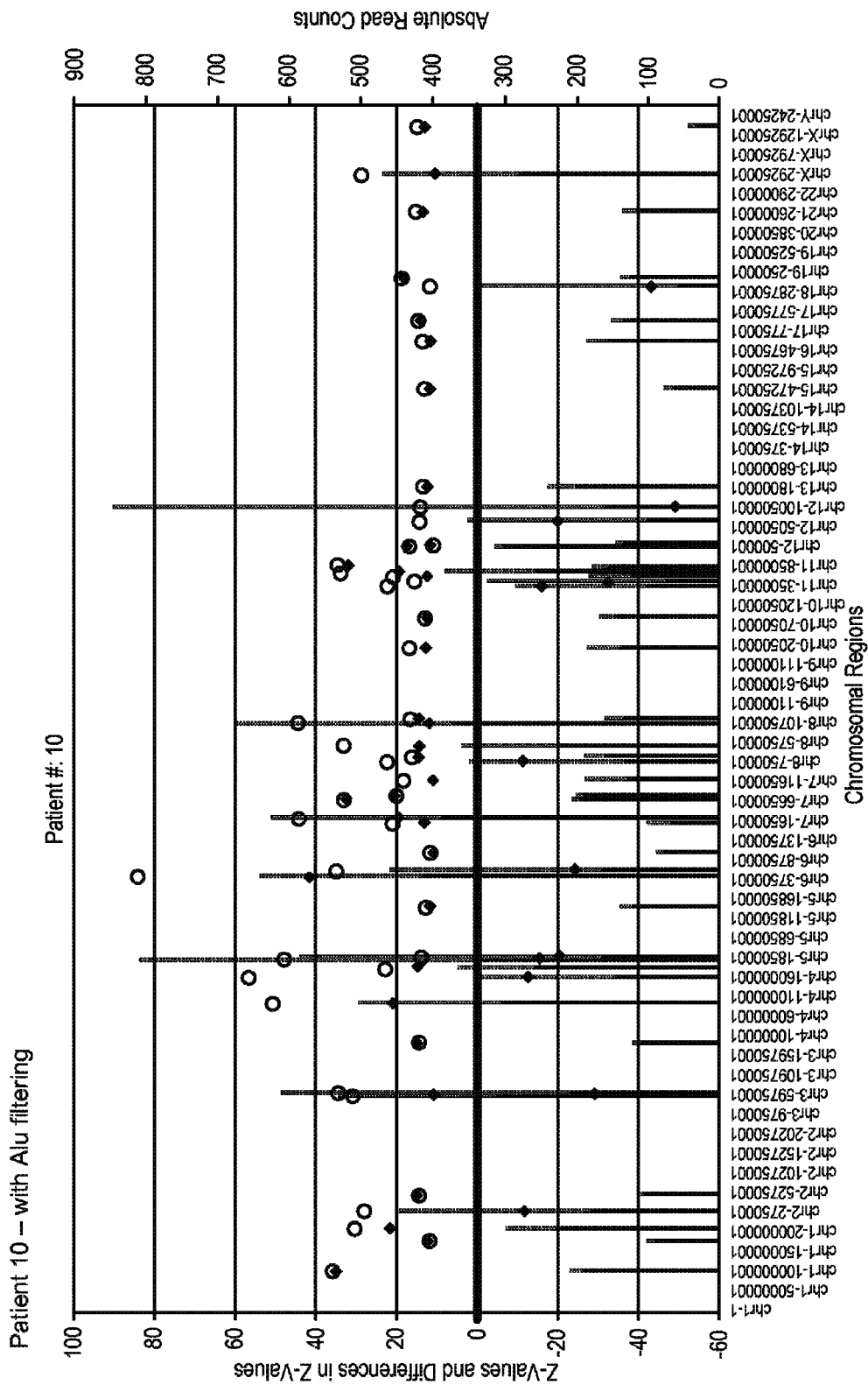
Figure 1:
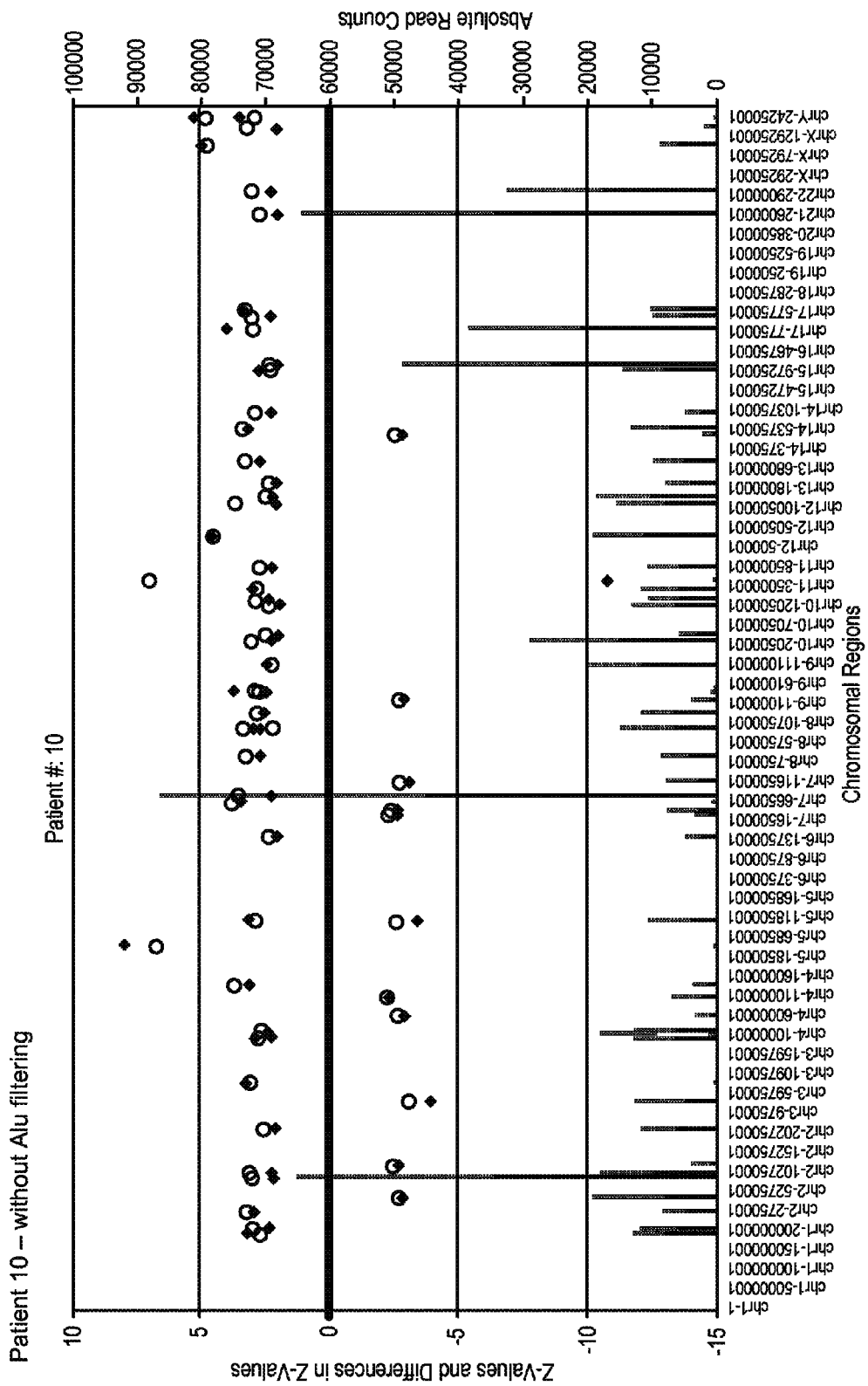
Figure 1:
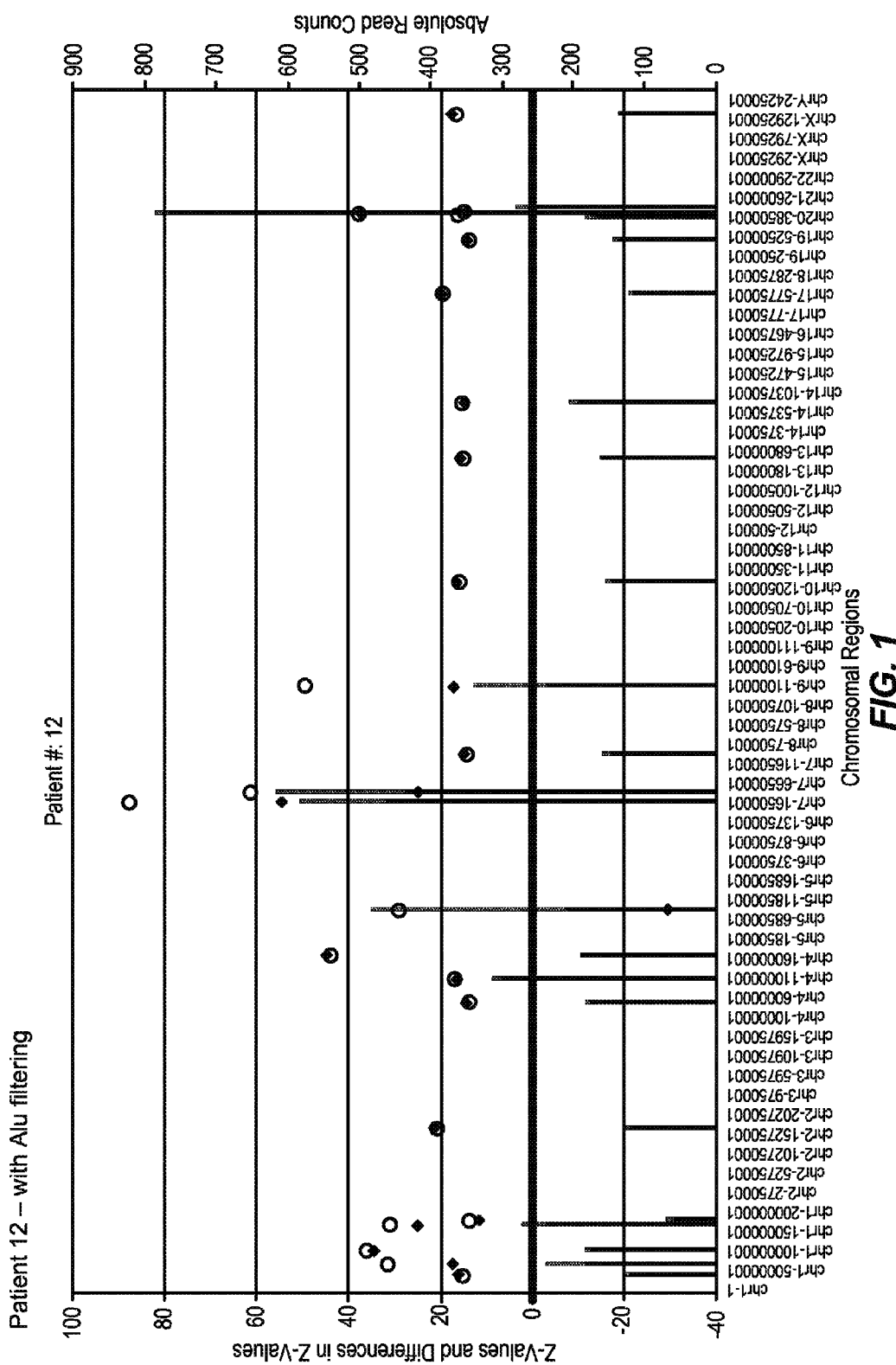
Figure 1:
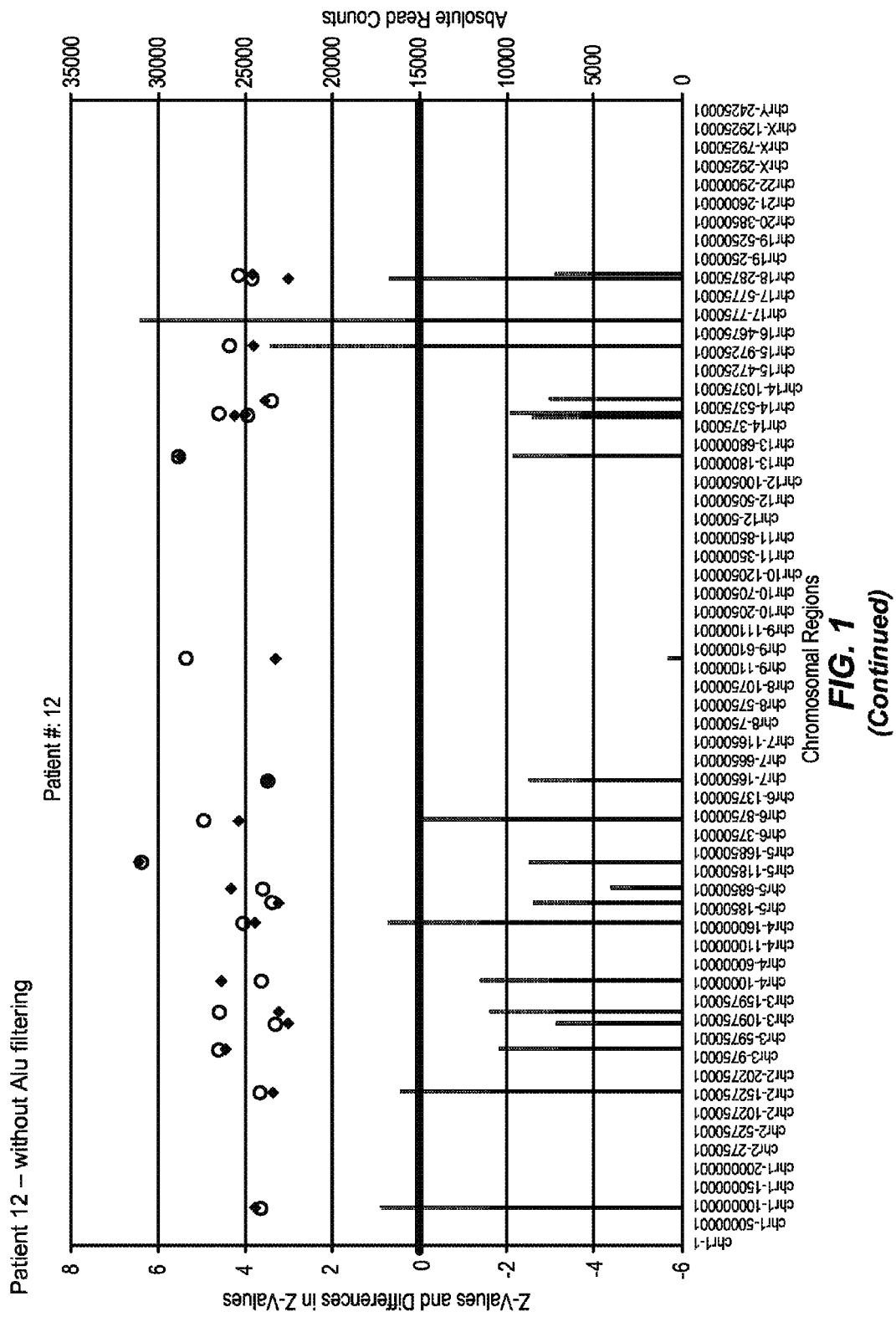
Figure 1:
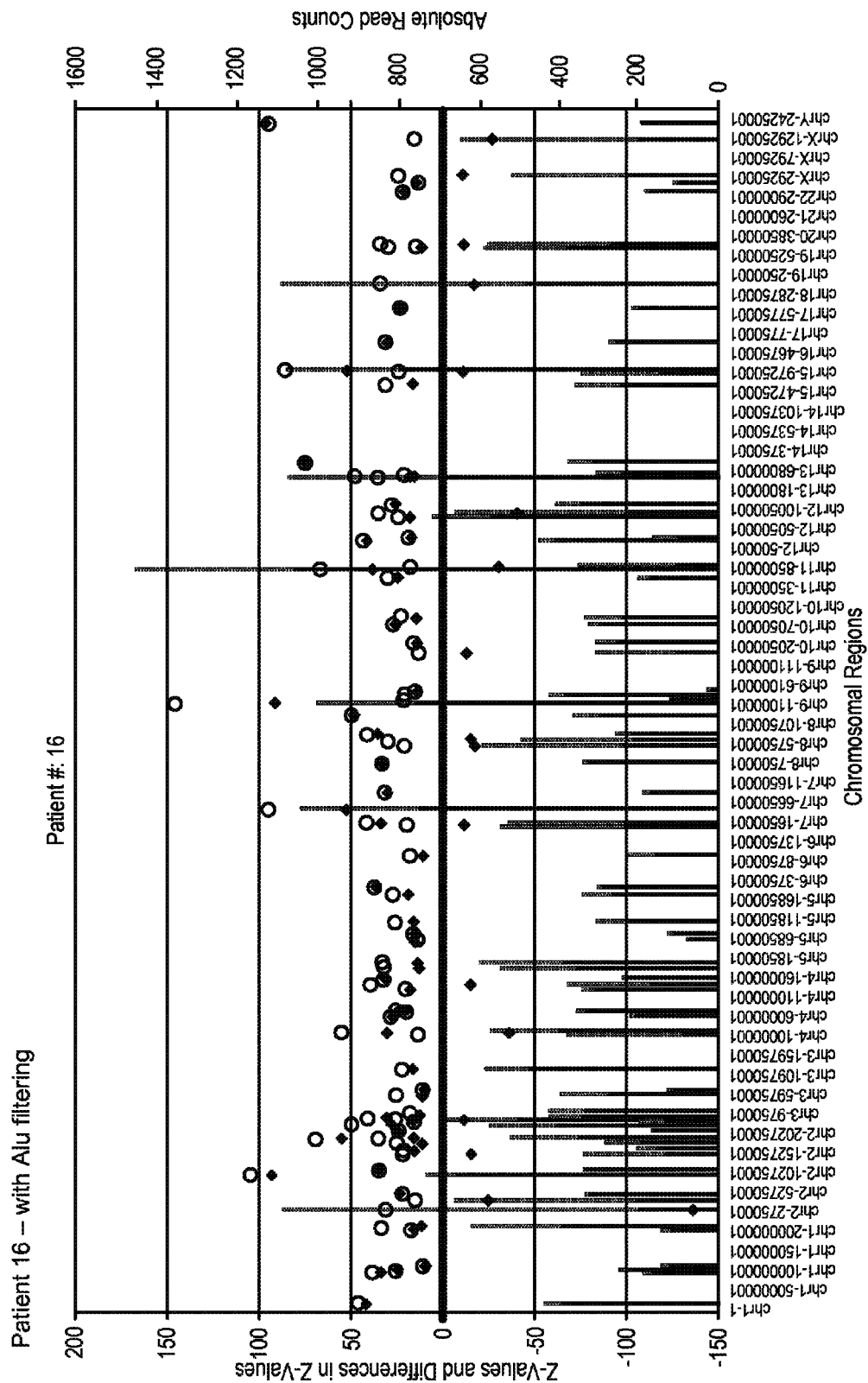
Figure 1:
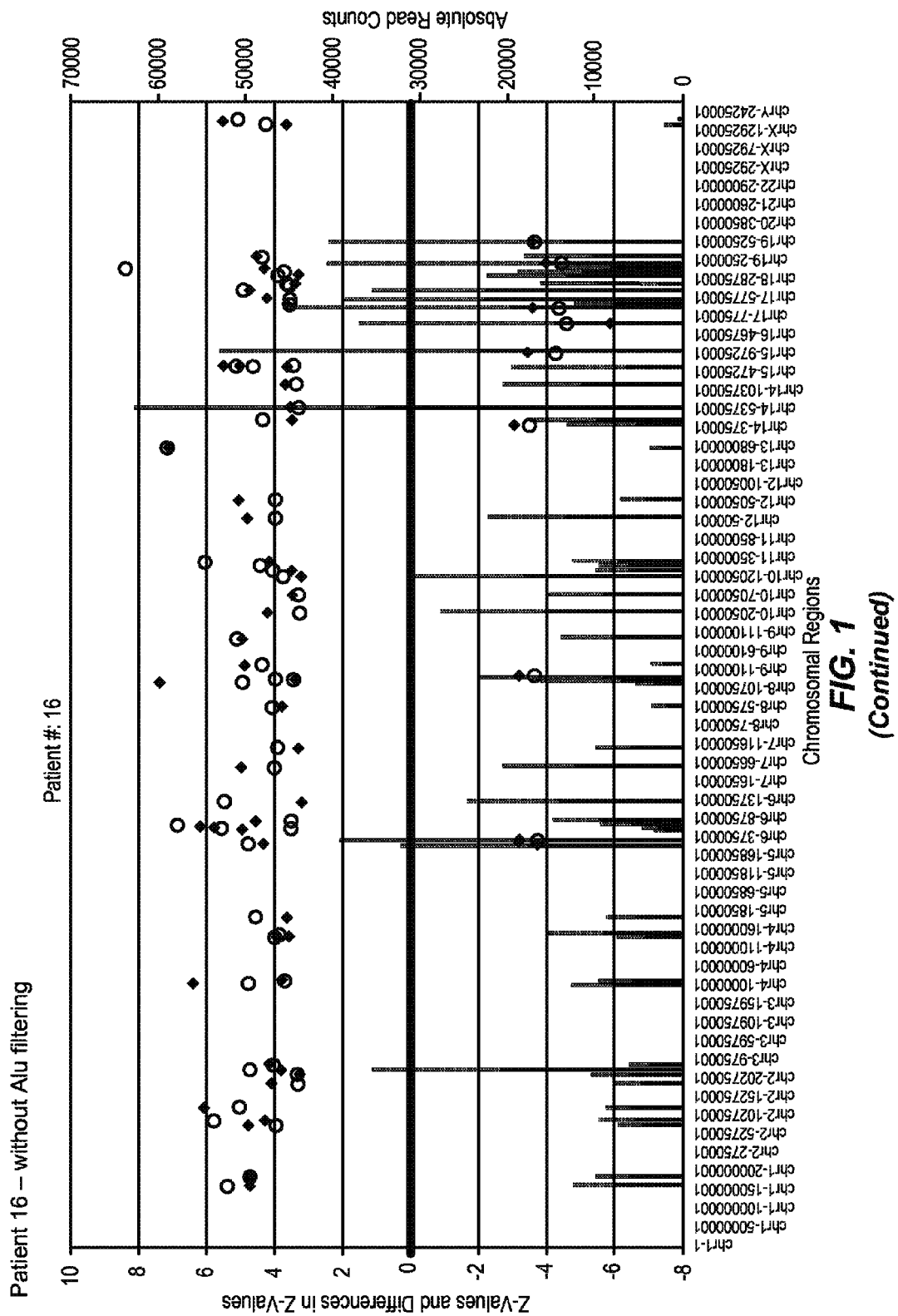

As used herein, a "biomarker" refers to a region of DNA that comprises repetitive element (e.g., Alu sequences, short interspersed nuclear elements (SINEs) and long interspersed nuclear elements (LINEs), or endogenous retroviruses (ERVs). Such a biomarker in the context of this invention is particular to a specific patient and is not present in normal DNA, e.g., DNA from a peripheral blood sample from the patient, or is not present in the corresponding region of a normal human genome. An example of a reference normal human genome is the *Homo sapiens* (human) genome, hg18/build 36.1 genome version release March 2006.

The term "unambiguously assigned" or "uniquely positioned to a defined region in a normal human genome" in the context of this invention refers to determining that a sequence read obtained from either circulating cell-free DNA or tumor or peripheral blood mononuclear cells DNA can be assigned to a particular region of the reference genome. In determining a personalized biomarker, a sequence is assigned to a particular region in the reference genome based on well-known algorithms for identity, such as the BLAST algorithm using high stringent parameters, such as e<0.0001. In addition, such a sequence does not have a further equally fitting hit on the reference genome that is employed. For example, in embodiments regarding human patients, the reference genome is typically a human genome build from the human genome database.

The term "circulating cell-free DNA" as used herein means free DNA molecules of 25 nucleotides or longer that are not contained within any intact cells in human blood, and can be obtained from human serum or plasma.

The term "primer" refers to an oligonucleotide that acts as a point of initiation of DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature. A primer is preferably a single-stranded oligodeoxyribonucleotide. The primer includes a "hybridizing region" exactly or substantially complementary to the target sequence, preferably about 15 to about 35 nucleotides in length. A primer oligonucleotide can either consist entirely of the hybridizing region or can contain additional features which allow for the detection, immobilization, or manipulation of the amplified product, but which do not alter the ability of the primer to serve as a starting reagent for DNA synthesis. For example, a nucleic acid sequence tail can be included at the 5' end of the primer that hybridizes to a capture oligonucleotide.

The term "probe" refers to an oligonucleotide that selectively hybridizes to a target nucleic acid under suitable conditions. A probe for detection of the biomarker sequences described herein can be any length, e.g., from 15-500 bp in length. Typically, in probe-based assays, hybridization probes that are less than 50 bp are preferred.

The term "target sequence" or "target region" refers to a region of a nucleic acid that is to be analyzed and comprises the sequence of interest.

As used herein, the terms "nucleic acid," "polynucleotide" and "oligonucleotide" refer to primers, probes, and oligomer fragments. The terms are not limited by length and are generic to linear polymers of polydeoxyribonucleotides (containing 2-deoxy-D-ribose), polyribonucleotides (containing D-ribose), and any other N-glycoside of a purine or pyrimidine base, or modified purine or pyrimidine bases. These terms include double- and single-stranded DNA, as well as double- and single-stranded RNA. Oligonucleotides for use in the invention may be used as primers and/or probes.

A nucleic acid, polynucleotide or oligonucleotide can comprise phosphodiester linkages or modified linkages including, but not limited to phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages.

A nucleic acid, polynucleotide or oligonucleotide can comprise the five biologically occurring bases (adenine, guanine, thymine, cytosine and uracil) and/or bases other than the five biologically occurring bases. These bases may serve a number of purposes, e.g., to stabilize or destabilize hybridization; to promote or inhibit probe degradation; or as attachment points for detectable moieties or quencher moieties. For example, a polynucleotide of the invention can contain one or more modified, non-standard, or derivatized base moieties, including, but not limited to, N6-methyladenine, N6-tert-butyl-benzyl-adenine, imidazole, substituted imidazoles, 5-fluorouracil, 5 bromouracil, 5-chlorouracil, 5-iodouracil, hypoxanthine, xanthine, 4-acetylcytosine, 5 (carboxyhydroxymethyl)uracil, 5 carboxymethylaminomethyl-2-thiouridine, 5 carboxymethylaminomethyluracil, dihydrouracil, beta-D-galactosylqueosine, inosine, N6 isopentenyladenine, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2 thiocytosine, 5-methyl-2-thiouracil, 2-thiouracil, 4-thiouracil, 5-methyluracil, uracil-5-oxyacetic acidmethylester, 3-(3-amino-3-N-2-carboxypropyl) uracil, (acp3)w, 2,6-diaminopurine, and 5-propynyl pyrimidine. Other examples of modified, non-standard, or derivatized base moieties may be found in U.S. Pat. Nos. 6,001,611; 5,955,589; 5,844,106; 5,789,562; 5,750,343; 5,728,525; and 5,679,785, each of which is incorporated herein by reference in its entirety. Furthermore, a nucleic acid, polynucleotide or oligonucleotide can comprise one or more modified sugar moieties including, but not limited to, arabinose, 2-fluoro-arabinose, xylulose, and a hexose.

"Repetitive sequences or repetitive elements" refer to highly repeated DNA elements present in a genome. These sequences are usually categorized in sequence families and are broadly classified as interspersed repetitive DNA (see, e.g., Jelinek and Schmid, Ann. Rev. Biochem. 51:831-844, 1982; Hardman, Biochem J. 234:1-11, 1986; and Vogt, Hum. Genet. 84:301-306, 1990) or tandemly repeated DNA. Repetitive elements include satellite, minisatellite, and microsatellite DNA. In humans, interspersed repetitive DNA includes Alu sequences, short interspersed nuclear elements (SINE) and long interspersed nuclear elements (LINEs), and endogenous retroviruses (ERVs). The categorization of repetitive elements and families of repetitive elements and their reference consensus sequences are defined in public databases (e.g., repbase (version 18.10)— Genetic Information Research Institute (Jurka et al., Cytogenet Genome Res 2005; 110:462-7)).

The term "Alu sequence" or "Alu repeated sequence" refers to a sequence that is categorized as a member of a family of conserved, short interspersed elements of genomic DNA. There are about 1,000,000 copies of Alu-repetitive DNA sequences in the human genome (see, e.g., Rowald and Herrera (2000) Genetics 108:57-72). A typical Alu is a dimer, built of two similar sequence elements (left and right arms) that are separated by a short A-rich linker. Most Alu sequences have a long poly-A tail of about 20-100 bases. Alu sequences are named after the AluI restriction enzyme site within the consensus Alu sequence. Properties and the molecular origin of Alu-repetitive sequences are described, for example, in Mighell el al., FEBS Lett. 417:1-5, 1997 and Batzer et al., J. Mol Evol. 42:3-6, 1996. As known in the art, there may be slight variations in Alu sequences between different representative cell clones of a particular cell type, or between different representative organisms of the same species. Thus, as used herein, "Alu consensus sequences" or refers to sequences derived from multiple sequence alignment of different Alu sequences obtained from the same species or the same cell, wherein the Alu consensus sequences comprises the sequence of nucleotides in common or most common between the represented clones.

In the methods of the present inventions, an "Alu primer" refers to an oligonucleotide that hybridizes to an Alu sequence or an Alu consensus sequence and that in conjunction with another primer, can amplify Alu-containing sequences in amplification reactions.

SVA (Sine, VNTR, Alu) elements are repetitive mobile elements in the human genome. A typical SVA is flanked by target site duplications and comprise a variable number of hexameric repeats, a region with homology to antisense Alu sequence, a variable of tandem repeats a SINE-R region and a poly-A signal (see, e.g., Ostertag, et al., Am J Hum Genet 73(6): 1444-1451, 2003)

A "universal" priming site is a site to which a universal primer will hybridize. In general, "universal" refers to the use of a single primer or set of primers for a plurality of amplification reactions. For example, in using a universal primer for sequencing circulating cell-free DNA, the DNA is fragmented and adapted to contain a universal priming sequence to allow for sequencing and/or amplification of the circulating DNA using a single set of.

As used herein, the singular forms "a," "an" and "the" include plural referents unless the context clearly dictates otherwise. Thus, for example, reference to "a molecule" includes a plurality of such molecules, and the like.

Introduction

The invention is based, at least in part, on the discovery that chromosomal regions that contain repetitive sequences can be identified in circulating cell-free DNA in patients having a tumor. Such sequences provide personalized biomarkers that can be used to monitor the response of a cancer patient to therapy.

Accordingly, in one aspect, the invention provides a method of analyzing cell-free nucleic acids in a sample (blood, serum or plasma) from a cancer patient comprising determining personalized biomarkers for the patient. In a further aspect, the invention provides methods of using such personalized biomarkers.

Detection of Personalized Biomarkers

Library Preparation

In the typical embodiment, a library of DNA fragments obtained from nucleic acid samples from the various patent sources is prepared. These samples typically include a tumor sample, a sample from normal tissue, e.g., peripheral blood mononuclear cells; and cell-free nucleic acid samples obtained from prior to treatment with a therapeutic regiment and after treatment with the therapeutic regimen. For cell-free nucleic acid samples, the samples are obtained from the blood, e.g., serum or plasma. Nucleic acids can be isolated from serum or plasma using well known techniques, see, e.g., the example sections. In the context of the current invention, the nucleic acid sequences that are analyzed are DNA sequences.

The libraries are prepared from the DNA isolated from the samples using known techniques. In the case of DNA isolated from cells, the DNA may be fragmented to ensure an average size suitable for subsequent analysis (e.g., about 200 bp). Typically, DNA fragments are modified to contain adapter sequences with (universal) primer binding sites to allow amplification of the library. Adapters and barcodes (see below) for use in molecular biology library preparation techniques are well known to those of skill in the art. A universal primer binds to such an adapter sequence so that universal amplification of the adapter-ligated target sequences.

Universal primers and primer binding sites are well known in the art. These are often used in library construction to produce DNA fragments with known ends that can be used for further processing, e.g., sequencing. Universal primers and adapters are commercially available. Examples are those employed in massive parallel sequencing using 454/Roche (e.g. Titanium), Lifetechnologies (SOLiD or Personal Genome Machine), or Illumina (HiSeq) sequencing platforms.

Identification of DNA Comprising Repetitive Elements Present in Patient Samples

DNA fragments comprising repetitive elements can be identified using a number of techniques well known to those of skill in the art. For example, PCR may be performed on the libraries to identify fragments present in the library that comprise repetitive sequences. For example, amplification can be performed using a primer that hybridizes to the repetitive element (e.g., an Alu sequence) as one of the amplification primers and a universal primer as the other primer. Alternatively, the desired DNA fragments can be identified using oligonucleotide probes specific to the target repetitive sequence. In some embodiments, the probes are labeled (e.g., with biotin) to allow for the subsequent enrichment of the desired fragments using a solid support (e.g., magnetic beads). In these embodiments, the enriched DNA fragments can be amplified using universal primers.

Preparation of primers and probes specific to any particular repetitive element is well within the skill of those of ordinary skill in the art. The sequence of a number of repetitive elements are well known in the art (see e.g., repbase (version 18.10)—Genetic Information Research Institute (Jurka et al., *Cytogenet Genome Res* 2005; 110: 462-7)). For example, Alu sequences are well known in the art. Individual Alu sequences in the human genome are on the average only 15 to 20% divergent from each other. PCR primers based on known Alu sequences, e.g., an Alu consensus sequence, can be selected based on known Alu sequences. Examples of consensus Alu sequences are provided in Batzer et al, 1996, supra; and Bennet et al., *Genome Res*. 18:1875-1883, 2008 each of which references is incorporated by reference. In typical embodiments, it can be beneficial to perform two amplification reactions for each library to identify the Alu-enriched insertion regions. One reaction employs a reverse Alu primer and an appropriate forward universal primer' and the second reaction employs a forward Alu primer and an appropriate reverse universal primer. For example, primers used for Alu-enrichment can be designed based on the multi-sequence alignment shown in Batzer. This multi-sequence alignment is an alignment of AluJ, AluSx, AluSq, AluSp, AluSc, AluY, AluYa5, AluYa8 and AluYb8 subfamily consensus sequences. A reverse primer can be selected based on conserved base pairs at the 5'-region of the aligned sequences, e.g., residues 22-43 in the multi-sequence alignment. A forward primer can be selected based on conserved base pairs at the 3'-region of the aligned sequences, e.g., the sequence between residues 259 and 283 of the same multi-sequence alignment. Both primers are designed to amplify all of the indicated subfamilies. In some embodiments, PCR primers are based on Alu subfamilies that are active, i.e., capable of transposition. Thus, for example, an alignment of AluS or AluY subfamily consensus sequences can be used to identify conserved regions in the desired subfamilies. As understood in the art, the primer sequence need not exactly match the Alu consensus sequence, so long as they can amplify Alu subfamilies of interest. Typical primer sequences are at least 20 nucleotides, preferably 25, 30, 35, 40, 45, or 50, or greater nucleotides, in length. In some embodiments, an Alu primer for use in the invention comprises a nucleotide sequence of SEQ ID NO:5 or 6, or has at least 75% identity, typically at least 80%, 85%, 90%, 95%, or greater, identity to SEQ ID NO:5 or SEQ ID NO:6.

Similarly, sequence information for SINEs, LINEs, and ERVs is readily available. As noted above, the categorization of repetitive elements and families of repetitive elements and their reference consensus sequences are defined in public databases (e.g., repbase (version 18.10)—Genetic Information Research Institute (Jurka et al., *Cytogenet Genome Res* 2005; 110:462-7)).

The amplified products are then sequenced and the sequences evaluated to identify regions that have an repetitive element-insertion. As understood in the art, the amplified products can be subjected to manipulations, e.g., adding molecular barcodes, to facilitate sequencing procedures.

DNA Sequencing

Detection of individual biomarkers in accordance with the invention comprises sequencing DNA isolated from various patient samples, e.g., cell-free nucleic acids present in the blood, DNA isolated from a patient tumor, etc. Such sequencing can be performed using known sequencing methodologies, e.g., Illumina, Lifetechnologies, and Roche 454 sequencing systems. In typical embodiments, cell-free DNA, or DNA isolated from a patient tumor, or non-tumor tissues, e.g., peripheral blood mononuclear cells, from a patient is sequenced using a large-scale sequencing method that provides the ability to obtain sequence information from many reads. Such sequencing platforms include those commercialized by Roche 454 Life Sciences (GS systems), Illumina (e.g., HiSeq, MiSeq) and Lifetechnologies (e.g., SOLiD systems).

The Roche 454 Life Sciences sequencing platform involves using emulsion PCR and immobilizing DNA fragments onto bead. Incorporation of nucleotides during synthesis is detected by measuring light that is generated when a nucleotide is incorporated.

The Illumina technology involves the attachment of randomly fragmented genomic DNA to a planar, optically transparent surface. Attached DNA fragments are extended and bridge amplified to create an ultra-high density sequencing flow cell with clusters containing copies of the same template. These templates are sequenced using a sequencing-by-synthesis technology that employs reversible terminators with removable fluorescent dyes.

Methods that employ sequencing by hybridization may also be used. Such methods, e.g., used in the Lifetechnologies SOLiD4+ technology uses a pool of all possible oligonucleotides of a fixed length, labeled according to the sequence. Oligonucleotides are annealed and ligated; the preferential ligation by DNA ligase for matching sequences results in a signal informative of the nucleotide at that position.

The sequence can be determined using any other DNA sequencing method including, e.g., methods that use semiconductor technology to detect nucleotides that are incorporated into an extended primer by measuring changes in current that occur when a nucleotide is incorporated (see, e.g., U.S. Patent Application Publication Nos. 20090127589 and 20100035252). Other techniques include direct label-free exonuclease sequencing in which nucleotides cleaved from the nucleic acid are detected by passing through a nanopore (Oxford Nanopore) (Clark et al., *Nature Nanotechnology* 4: 265-270, 2009); and Single Molecule Real Time (SMRT™) DNA sequencing technology (Pacific Biosciences), which is a sequencing-by synthesis technique.

Detection of Personal Biomarker Insertion Regions

For each DNA sample, the DNA is sequenced and evaluated for the presence of repetitive element insertion sequences. In identifying repetitive element insertion regions that can be used as personalized biomarkers, all sequences that map within a window of about 250 base pairs in the vicinity of repetitive element (e.g., Alu, SVA elements, or LINEs) annotated in the reference genome are typically removed from consideration as a candidate insertion sequence using applications such as RepeatMasker. For the remaining sequences, insertion regions comprising repetitive sequences are identified. One of skill understands that insertions regions can be defined using various criteria. In one embodiment, insertion regions are defined as those fragments that have sequences originating from the amplification reaction employing the reverse Alu primer that falls together within a 200 base pair window of a sequence originating from the Alu forward PCR primer.

Various filtering procedures are then employed to determine those insertion regions that are tumor biomarkers for the particular patient. In one embodiment, an Alu-insertion regions is an individualized biomarker when it has the following properties: it is present in a tumor sample from a patient, but not in normal samples, and it is present in a pre-therapy cell-free nucleic acid sample from the patient, but not a post-therapy cell-free nucleic acid sample from the patient.

In some embodiments, a direct comparison of various samples from the patient is performed. For examples, the following comparisons can be made to identify biomarkers. Repetitive element insertion regions identified in the DNA from a tumor sample from the patient is compared to the insertion regions identified in the DNA from normal controls. The normal sample may be a non-tumor sample from the patient and/or one or more samples from normal individuals (i.e., individuals not diagnosed with cancer). In some embodiments, the normal sample is from non-tumor tissue from the patient, e.g., from peripheral blood mononuclear cells. Those repetitive element insertion regions that are present in a tumor sample, but not in normal DNA, are also compared to those present in pre-therapy cell-free DNA samples obtained from the patients. Repetitive element insertion regions that are present in both the tumor sample and pre-therapy samples are compared to the insertion regions contained in a post-therapy cell-free DNA sample obtained from the patient. Those insertion regions that are present in both the tumor sample and pre-therapy cell-free DNA sample are then compared to insertion regions that are detected in a post-therapy cell-free DNA sample. Those insertion regions that are not present in the post-therapy sample are biomarkers for that individual patient. One of skill in the art understands that these comparisons need not be performed in any particular order.

The comparisons can be performed in a semi-quantitative or quantitative manner. Thus, for example, in a semi-quantitative approach the presence or absence of the insertion regions in a sample is simply identified as a positive or negative when determining a biomarker. Alternatively more quantitative procedures can be employed to identify biomarkers. In some embodiments, the comparison between the insertion regions detected in the tumor sample to insertion regions detected in normal samples, from that patient and independent normal controls, can be quantitative. For example, the methods of identifying a biomarker may comprise a comparison step where only those regions are considered as potential biomarkers where the normalized count in the PBMC differs at least 5-fold compared to the tumor DNA. One of skill understands that factors other than "5-fold", e.g., 2 to 4-fold, or 6-fold or higher, can be used in such a quantitative analysis. The same type of quantitative comparison can be also applied to evaluating post-therapy insertion regions.

Another aspect of a quantitative approach is to set limits for the comparisons between the tumor vs. normal repetitive element insertion regions and the tumor insertion regions to the pre-therapy insertion regions where a minimal analytical coverage per found region can be considered as criterion. For example, insertions to a defined genomic position that are only seen in a tumor sample, but not in a normal, non-cancerous control, are considered if such an insertion is found in sequencing in at least three instances. This number can be set on any number >0. Any combination of quantitative and qualitative means of filtering may be employed.

In evaluating the cell-free DNA samples, one of skill understands that the sequences from the pre-therapy and post-therapy samples are typically compared to those from a set of normal controls. For any comparison, the results obtained by a defined method can be compared to results obtained by the same methodological approach, but using a different sample or sets of samples. Such comparison samples can come from normal control individuals, e.g., plasma or serum sample from normal control individuals. Such a group of individuals without cancer are typically deemed a "reference group". Samples obtained from such a reference group can be used as defined reference samples for transversal comparisons. In instances when normal somatic cells from an individual are available, such cells can be defined as a reference for an intra-individual comparison. Using a "timed" sample (e.g., pre therapy that can be compared to a post-therapy sample as a reference) allows for an intra-individual (longitudinal) comparison.

Once an insertion region is identified that can serve as a personalized biomarker, the region is sequenced to facilitate use of the marker as described below.

Use of the Personalized Biomarkers

A personalized biomarker identified in accordance with the invention may be used to evaluate response of that particular patient to a cancer therapy. Such an evaluation can be performed, e.g., using an amplification reaction and/or nucleic acid hybridization to detect the levels of the personalized biomarker in the cell-free nucleic acids present in a blood sample from the patient.

In order to detect the presence of the personalized biomarker, a blood sample is obtained from the patient before and/or after treatment with a cancer therapy. Serum or plasma from the blood sample is then analyzed for the presence of the personalized biomarker.

Detection techniques for evaluating nucleic acids for the presence of a personalized biomarker involve procedures well known in the field of molecular genetics. In typical embodiments, detection of a personalized biomarker involves amplification of nucleic acids. Ample guidance for performing such techniques is provided in the art. Exemplary references include manuals such as PCR Technology: *Principles and Applications for DNA Amplification* (ed. H. A. Erlich, Freeman Press, NY, N.Y., 1992); *PCR Protocols: A Guide to Methods and Applications* (eds. Innis, et al., Academic Press. San Diego, Calif., 1990); Current Protocols in Molecular Biology, Ausubel, 1994-1999, including supplemental updates through April 2004; Sambrook & Russell, *Molecular Cloning, A Laboratory Manual* (3rd Ed, 2001).

Although the methods may employ PCR steps, other amplification protocols may also be used. Suitable amplification methods include ligase chain reaction (see, e.g., Wu & Wallace, *Genomics* 4:560-569, 1988); strand displacement assay (see, e.g., Walker et al., *Proc. Natl. Acad. Sci. USA* 89:392-396, 1992; U.S. Pat. No. 5,455,166); and several transcription-based amplification systems, including the methods described in U.S. Pat. Nos. 5,437,990; 5,409,818; and 5,399,491; the transcription amplification system (TAS) (Kwoh et al., *Proc. Natl. Acad. Sci. USA* 86:1173-1177, 1989); and self-sustained sequence replication (3SR) (Guatelli et al., *Proc. Natl. Acad. Sci. USA* 87:1874-1878, 1990; WO 92/08800). Alternatively, methods that amplify the probe to detectable levels can be used, such as Qβ-replicase amplification (Kramer & Lizardi, *Nature* 339:401-402, 1989; Lomeli et al., *Clin. Chem.* 35:1826-1831, 1989). A review of known amplification methods is provided, for example, by Abramson and Myers in *Current Opinion in Biotechnology* 4:41-47, 1993.

In some embodiments, oligonucleotide primers are employed that amplify the biomarker of interest. The presence of the biomarker can be determined, for example by detecting the length of the biomarker in the cell-free nucleic acid in comparison to a control. In other embodiments, a probe may also be used to detect the presence of the biomarker.

Oligonucleotides that are employed as primers and/or probes to detect biomarkers can be selected using methods well-known in the art. For example, PCR primers may be designed using standard primer design computer software techniques known to individuals skilled in the art. The variables considered during PCR primer design may include primer length, GC pair content, melting temperature, and size of the target nucleic acid amplified by the primer pair.

In one embodiment, the biomarker is identified by hybridization under sequence-specific hybridization conditions with a probe that targets the biomarker region (e.g., targets some unambiguously assigned portion of, the target biomarker).

Suitable hybridization formats are well known in the art, including but not limited to, solution phase, solid phase, oligonucleotide array formats, mixed phase, or in situ hybridization assays. In solution (or liquid) phase hybridizations, both the target nucleic acid and the probe or primers are free to interact in the reaction mixture. Techniques such as real-time PCR systems have also been developed that permit analysis, e.g., quantification, of amplified products during a PCR reaction. In this type of reaction, hybridization with a specific oligonucleotide probe occurs during the amplification program to identify the presence of a target nucleic acid. Hybridization of oligonucleotide probes ensure the highest specificity due to thermodynamically controlled two state transition. Examples for this assay formats are fluorescence resonance energy transfer hybridization probes, molecular beacons, molecular scorpions, and exonuclease hybridization probes (e.g., reviewed in Bustin, *J. Mol. Endocrin.* 25:169-93, 2000).

Either the probe or target sequence can be immobilized. For example, the probe may comprise a label (e.g., biotin) that allows the probe and target sequence to be captured on a solid support (e.g., a magnetic bead).

In a format where the target is immobilized, amplified target DNA is immobilized on a solid support and the target complex is incubated with the probe under suitable hybridization conditions, unhybridized probe is removed by washing under suitably stringent conditions, and the solid support is monitored for the presence of bound probe. In formats where the probes are immobilized on a solid support, the target DNA is typically labeled, usually during amplification. The immobilized probe is incubated with the amplified target DNA under suitable hybridization conditions, unhybridized target DNA is removed by washing under suitably stringent conditions, and the solid support/probe is monitored for the presence of bound target DNA.

In some embodiments, multiple probes, e.g., that target different biomarkers for that patient, are immobilized on a solid support and the cell-free DNA from a patient is analyzed using the multiple probes simultaneously. Examples of nucleic acid arrays are described by WO 95/11995.

In an alternative probe-less method, amplified nucleic acid corresponding to a target nucleic acid is performed using nucleic acid primers to the chromosomal region and is detected by monitoring the increase in the total amount of double-stranded DNA in the reaction mixture, is described, e.g., in U.S. Pat. No. 5,994,056; and European Patent Publication Nos. 487,218 and 512,334. The detection of double-stranded target DNA relies on the increased fluorescence various DNA-binding dyes, e.g., SYBR Green, exhibit when bound to double-stranded DNA.

Oligonucleotides can be prepared by any suitable method, usually chemical synthesis, and can also be purchased through commercial sources. Oligonucleotides can include modified phosphodiester linkages (e.g., phosphorothioate, methylphosphonates, phosphoamidate, or boranophosphate) or linkages other than a phosphorous acid derivative into an oligonucleotide may be used to prevent cleavage at a selected site. In addition, the use of 2'-amino modified sugars tends to favor displacement over digestion of the oligonucleotide when hybridized to a nucleic acid that is also the template for synthesis of a new nucleic acid strand.

In some embodiments, the level of the biomarker in the patient circulating CAN is determined relative to an index value, such as the amount of the biomarker that is identified in normal controls.

Devices and Kits

In a further aspect, the invention provides kits useful for identifying one or more individualized biomarkers in the cell-free circulating nucleic acid from a patient. In one aspect, the kit provides at least one Alu primer and a universal primer and/or adapters to ligate a universal primer binding site to fragmented cell-free circulating DNA from the patient. Such reagents can be used to identify individual biomarkers.

Determination of a Personalized Cancer Biomarker

In the context of the invention, "detection" or "identification" or "identifying the presence" or "detecting the presence" of a personalized in a circulating cell-free nucleic acid sample from a patient refers to determining any level of the biomarker in the circulating nucleic acid sample from the patient. Once a biomarker is detected, the information can be used to assist in evaluating the response of a patient to a therapy. For example, the presence of an individualized biomarker in circulating cell-free DNA in the patient following treatment with a particular therapeutic protocol may indicate that the patient has not completely responded to the protocol. Accordingly, the information may be used to assist in determining adjustments to the therapeutic protocol and/or to determine if an alternative therapy should be employed.

The information obtained from the biomarker analysis may be stored in a computer readable form. Such a computer system typically comprises major subsystems such as a central processor, a system memory (typically RAM), an input/output (I/O) controller, an external device such as a display screen via a display adapter, serial ports, a keyboard, a fixed disk drive via a storage interface and a floppy disk drive operative to receive a floppy disc, and a CD-ROM (or DVD-ROM) device operative to receive a CD-ROM. Many other devices can be connected, such as a network interface connected via a serial port.

The computer system may also be linked to a network, comprising a plurality of computing devices linked via a data link, such as an Ethernet cable (coax or 10BaseT) telephone line, ISDN line, wireless network, optical fiber, or other suitable signal transmission medium, whereby at least one network device (e.g., computer, disk array, etc.) comprises a pattern of magnetic domains (e.g., magnetic disk) and/or charge domains (e.g., an array of DRAM cells) composing a bit pattern encoding data acquired from an assay of the invention.

The computer system can comprise code for interpreting the results of a study to determine personalized biomarkers or to evaluating the presence of one or more of the personalized biomarkers identified in accordance with the invention to aid in prognosis. Thus in an exemplary embodiment, the biomarker analysis results are provided to a computer where a central processor executes a computer program for evaluating the one or more biomarkers.

The invention also provides the use of a computer system, such as that described above, which comprises: (1) a computer; (2) a stored bit pattern encoding the biomarker testing results obtained by the methods of the invention, which may be stored in the computer; (3) and, optionally, (4) a program for valuating a biomarker.

The invention further provides methods of generating a report based on the detection of one or more personalized biomarkers for the patient.

Thus, the present invention provides systems related to the above methods of the invention. In one embodiment the invention provides a system for analyzing circulating cell-free DNA, comprising: (1) a sample analyzer for executing the method of analyzing circulating cell-free DNA in a patient's blood, serum or plasma as described in the various embodiments above; (2) a computer system for automatically receiving and analyzing data obtained in step (1) to provide a test value representing the status (presence or absence or amount, i.e., concentration or copy number) of a personalized biomarker for the patient.

The computer-based analysis function can be implemented in any suitable language and/or browsers. For example, it may be implemented with C language and preferably using object-oriented high-level programming languages such as Visual Basic, SmallTalk, C++, and the like. The application can be written to suit environments such as the Microsoft Windows™ environment including Windows™ 98, Windows™ 2000, Windows™ NT, and the like. In addition, the application can also be written for the MacIntosh™, SUN™, UNIX or LINUX environment. In addition, the functional steps can also be implemented using a universal or platform-independent programming language. Examples of such multi-platform programming languages include, but are not limited to, hypertext markup language (HTML), JAVA™, JavaScript™, Flash programming language, common gateway interface/structured query language (CGI/SQL), practical extraction report language (PERL), AppleScript™ and other system script languages, programming language/structured query language (PLUSQL), and the like. Java™- or JavaScript™-enabled browsers such as HotJava™, Microsoft™ Explorer™, or Netscape™ can be used. When active content web pages are used, they may include Java™ applets or ActiveX™ controls or other active content technologies.

The analysis function can also be embodied in computer program products and used in the systems described above or other computer- or internet-based systems. Accordingly, another aspect of the present invention relates to a computer program product comprising a computer-usable medium having computer-readable program codes or instructions embodied thereon for enabling a processor to carry out the analysis and correlating functions as described above. These computer program instructions may be loaded onto a computer or other programmable apparatus to produce a machine, such that the instructions which execute on the computer or other programmable apparatus create means for implementing the functions or steps described above. These computer program instructions may also be stored in a computer-readable memory or medium that can direct a computer or other programmable apparatus to function in a particular manner, such that the instructions stored in the computer-readable memory or medium produce an article of manufacture including instruction means which implement the analysis. The computer program instructions may also be loaded onto a computer or other programmable apparatus to cause a series of operational steps to be performed on the computer or other programmable apparatus to produce a computer implemented process such that the instructions which execute on the computer or other programmable apparatus provide steps for implementing the functions or steps described above.

The following examples are provided by way of illustration only and not by way of limitation. Those of skill in the art will readily recognize a variety of non-critical parameters that could be changed or modified to yield essentially similar results.

EXAMPLES

Identification of Individualized Biomarkers for Cancer

Example 1

This example describes the identification of individualized Alu biomarkers for breast cancer patients.
Sequencing Sequence libraries were prepared from tumor and peripheral blood mononuclear cells (PBMC) nuclear genomic DNA. Extracted genomic DNA (100 ng) was sheared by ultrasound to a size of about 200 bp. The fragments (50 ng) were end-repaired using 0.4 units/µL Klenow Fragment (USB, Affymetrics) and 0.2 units/µL Kinase (USB, Affymetrics) for 30 min at 37° C. The reaction was purified using AMPure beads (Angencourt). Single A-overhangs were attached to the end-repaired fragments by incubation with 0.4 units/µL of Klenow Fragment exo-(NEB) for 30 min at 37° C. The reaction was purified using AMPure beads (Agencourt). Adapters were ligated to the A-tailed fragments. The adapters were two single-stranded DNA oligonucleotides:

P9
(SEQ ID NO: 1)
gatcggaagagcatcgcaaggcaagcaagctaaaactgaaccgggttcc tcattagcg

P5
(SEQ ID NO: 2)
aatgatacggcgaccaccgagatctacactctttccctacacgacgctc ttccgatc*t

The P9 oligonucleotide has a 5-prime phosphate group. The P5 oligo has a phosphorothioate internucleotide linkage between the two 3-prime nucleotides, which is indicated by an asterisk. Both oligonucleotides were annealed to form a partially double stranded Y-adapter.

The Y-adapters were ligated to the A-tailed fragment by incubation with 1.2 units/µL ligase (USB, Affymetrics) for 30 min at room temperature. Adapter concentration in the reaction were 30× the molar amount of fragments ends. The reaction was purified using the SureClean Plus solution (Bioline).

The ligated fragments were amplified in 12 cycles of PCR using the primers:

P9-PCR-Primer
(SEQ ID NO: 3)
cgctaatgaggaacccggttcagttttagcttgcttgccttgcgatgct cttccgatc P5-Universal
(SEQ ID NO: 4)
aatgatacggcgaccaccgagatctacactctttccctacacgacgctc ttccgatct PCR reaction conditions were 200 µmol/L each dNTP, 0.02 units/µl Phusion High-Fidelity DNA Polymerase, 0.5 µmol/L each primer in 1× Phusion HF buffer. The cycling conditions were: 98° C. for 30 sec initial denaturation, 12 cycles of 98° C. for 10 sec, 62° C. for 30 sec, 70° C. for 30 sec and 70° C. for 5 min final elongation. The reaction was purified using the GenElute PCR Clean-Up Kit (Sigma-Aldrich).

Amplified library DNA (10 ng) was subjected to an Alu-enrichment PCR. The primers used in this PCR were:

Alu40.REV
(SEQ ID NO: 5)
gtgactggagttcagacgtgtgctcttccgatctcccaaagtgctggga ttacagg Alu259.FOR
(SEQ ID NO: 6)
gtgactggagttcagacgtgtgctcttccgatcggcracagagcgarac ycygtctca P5-Universal
(SEQ ID NO: 4)
aatgatacggcgaccaccgagatctacactctttccctacacgacgctc ttccgatct For each library, two PCRs using either primers Alu40.REV and P5-Universal or Alu259.FOR and P5-Universal were performed. PCR reaction conditions were 200 µmol/L each dNTP, 0.02 units/µl Phusion High-Fidelity DNA Polymerase, 1 µmol/L each primer in 1× Phusion HF buffer. Cycling conditions were: 98° C. for 30 sec initial denaturation, 12 cycles of 98° C. for 10 sec, 68° C. for 30 sec, 70° C. for 30 sec and 70° C. for 5 min final elongation. Reactions were purified using the innuPrep PCRpure Kit (Analytik Jena).

For each sample and each Alu-enrichment PCR, 200 ng of PCR-products were subjected to 4 cycles of PCR using fusion primers that carry an individual 7 bp index sequence. This sequence serves as molecular barcode allowing the assignment of each read to the respective sample and PCR after sequencing. The 3' part of the index-primers anneals to the underlined sequence of primer Alu40.REV and Alu259.FOR. The 5' part of this primer adds the full Illumina sequencing adapter to the fragments. The following is an example of a sequence of an index-primer: caagcagaagacg-gcatacgagat-7bpindex-gtgactggagttcagacgtgtgctcttccgatc. (SEQ ID NOs: 7 and 8)

Library preparation for the cell-free DNA fragments extracted from the patients' serum was performed as described for tumor and PBMC DNA, but the fragmentation step was omitted. The starting amount of cell-free DNA was 10 ng. The enriched library fragments from patients and from different samples were pooled and sequenced on an Illumina HiSeq or Illumina HiScan system according to the manufacturers protocols. Sequencing was conducted as single-read sequencing for 51 cycles followed by 8 cycles of index sequencing.
Bioinformatical Analyses Sequence reads were aligned to the human genome (HG18, NCBI36, March 2006) using the CASAVA software v1.8 (Illumina) with default parameterization. Using the repeat masked version of the human genome (HG18, NCBI36, March 2006), all sequence reads that map within a window of ±250 bp around an Alu or SVA element annotated in the reference genome were removed.

Of the remaining reads, insertion regions were constructed for each sample and each specimen. Insertion regions were defined by the following criteria: At least one read originating from the Alu40.REV PCR and at least one read originating from the Alu259.FOR PCR fall together within a 200 bp window. The region "start" is defined by the starting position of the first read. The region "stop" is defined by the end position of the last read. Start position, stop position, and number of reads were recorded for each insertion region of the respective sample and specimen.

Detection of Putative Tumor-Specific Insertion Regions

For each sample the insertion regions detected in the tumor were compared against all insertion regions detected in the PBMC genomes of all patients (n=17) and independent normal controls (n=8). All tumor insertion regions that overlapped (±200 bp) with regions detected in PBMC DNA were removed. For each patient, the remaining tumor insertion regions were compared against the insertion regions detected in the pre-surgery serum DNA of the respective patient. All tumor insertion regions that overlapped (±200 bp) with an insertion region detected in the pre-surgery serum were kept. All non-overlapping tumor regions were removed. For each patient, the remaining tumor insertion regions were compared against the insertion regions detected in the post-surgery serum DNA of the respective patient. All tumor insertion regions that overlapped (±200 bp) with an insertion region detected in the post-surgery serum were removed. All non-overlapping tumor regions were kept.

In an alternative approach, instead of filtering in the above mentioned qualitative manner (yes/no) a quantitative approach was designed, e.g., using a filter for the comparison. For example only those regions are kept where the normalized count in the PBMC differs by at least 5-fold compared to the tumor DNA. Other factors that can be used are 2- to 4-fold, or 6-fold or higher. The same quantitative comparison can be applied to the filtering described in filtering post-surgery insertion regions. Another aspect of a quantitative approach is to set limits for the comparisons between the tumor vs. normal Alu insertion regions and the tumor Alu insertions regions to the pre-therapy Alu insertions regions where a minimal read count per found region can be considered as criterion. Any combination of quantitative and qualitative means of filtering may be employed.

Sequence reads generated from the serum DNA pre-surgery and post-surgery and 24 additional apparently healthy individuals were subjected to depth of coverage analysis. Data were either used as such or reads that were mapped in a distance not greater than 200 bp next to an annotated ALU were omitted.

Mapped sequence reads were counted in windows of 250 kbp across the genome. Read counts were normalized to counts per 10 million reads Defining Regions with Significant Deviation from Normal Controls Using the window read counts of the 24 healthy control samples the upper and lower confidence limits were calculated by using a "leave one out" approach. Briefly, the Z-value was calculated for each bin with the remaining 23 normals as basis. The mean and standard deviation for each bin was then calculated using the 24 resulting data points (Z-values) for each window.

Window read counts of the pre-surgery specimens were selected as potential diagnostic regions of copy-number imbalance if outside the upper or lower confidence bounds. The deviation of each window read count for each pre- and post-surgery specimen from the average of the healthy control window read counts was expressed as Z-value (basis: 24 normals).

Comparison of Pre-Surgery Versus Post-Surgery Copy-Number Imbalances

Per patient, the genomic regions with significant copy-number imbalance in the pre-surgery serum sample were examined for significant imbalances in the post-surgery serum sample. For this, the difference between the windows Z-value of the post-surgery sample was subtracted from the windows Z-value of the pre-surgery sample. A highly positive or negative Z-value difference is indicative of an imbalanced region that is linked to the presence of the tumor, because it indicates a high deviation from the normal controls in the pre-surgery serum DNA, but a low deviation from the normal control in the post-surgery serum DNA.

Estimating Insertions into or in Close Vicinity to Repetitive Elements (RE)

Because a portion of ~20% of sequenced reads could not be uniquely mapped to the human genome, an alignment to the database of known human repeats was performed (Genetic Information Research Institute (GIRI) database). The resulting uniquely mapped reads were counted per database entry and normalized using the total number of mapped reads. The normalized read counts were then filtered for those that were different in tumor compared to the genomic PBMC DNA and in addition, different with respect to a comparison of pre- and post surgery serum CNA. For comparison tumor values, values are then converted to Z-values using the average of PBMC values and standard deviation from tumor values. For the serum values, the respective sample group served as basis (e.g., all pre-surgery data for pre-surgery results, all post-surgery data for post-surgery results).

Result for Depth of Coverage Analysis

FIG. 1 provides graphs showing the results for five 5 patients. The graphs were generated by a) with Alu filtering on (No Alus) and b) without. Normalized numbers of sequence reads obtained from cell-free circulation DNA that aligned to the human genomic database HG18 were summed into 250 kbp window bins. The results were converted into Z-values as described. For each such bin, pre-surgery values <3 were censored to zero. Circles represent the Z-value pre surgery, diamonds the difference between pre-surgery Z-value and post-surgery Z-values. The bars display the count sum that was used to calculate the Z-values for comparison.

Results for Detection of Putative Tumor-Specific Insertion Regions

Figure 2:
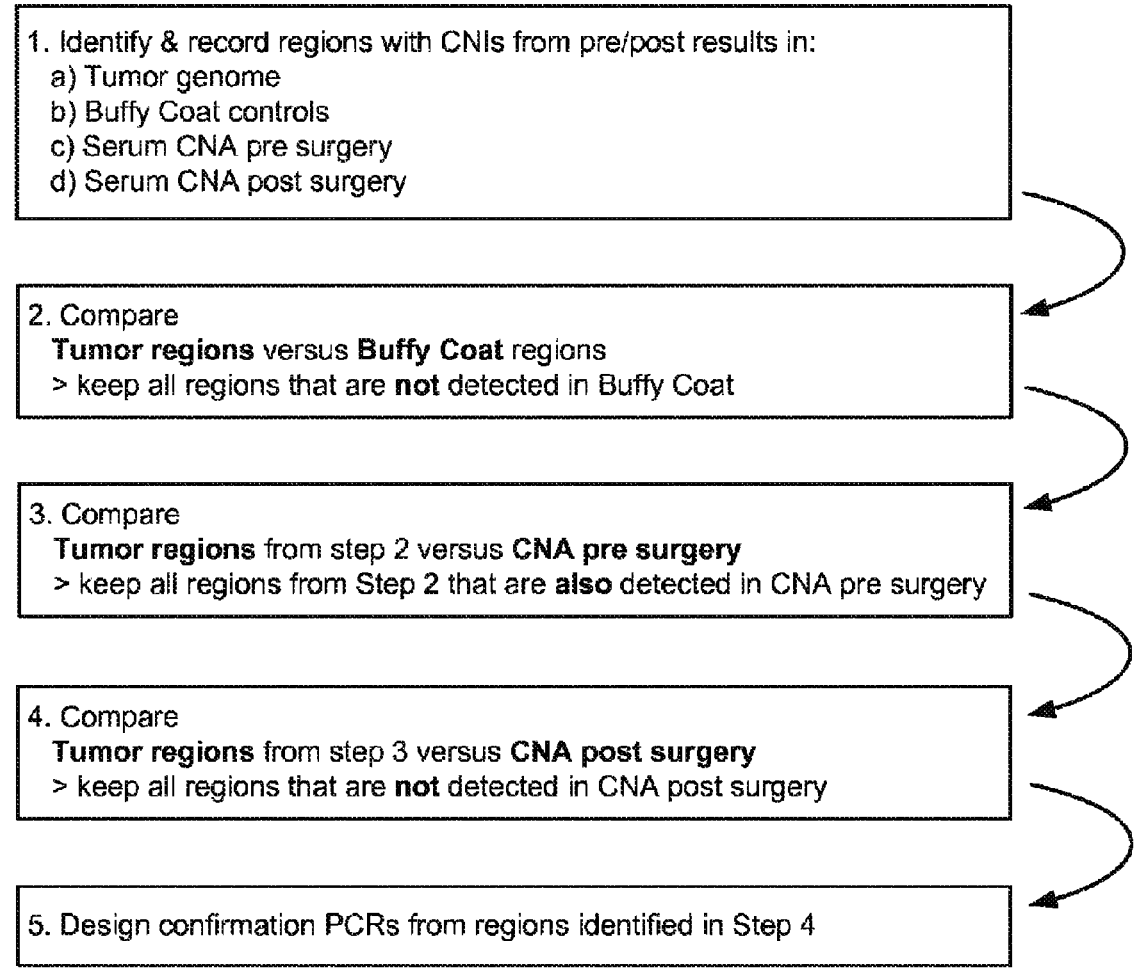
FIG. 2 show a flow diagram to illustrate a filtering algorithm used to identify regions that are likely to inherit Alu insertions specific to tumor cells.
Figure 3A:
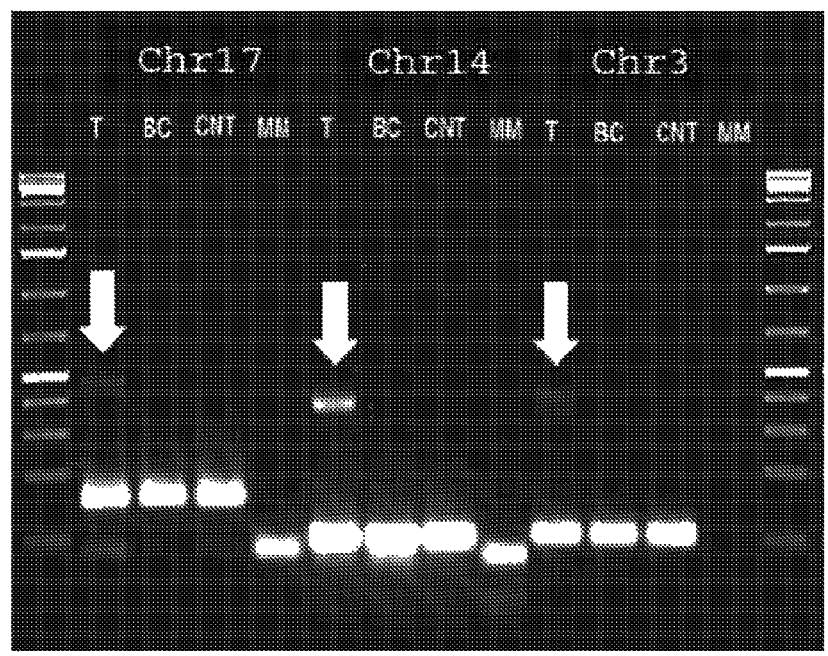
FIG. 3A to E shows agarose gel images illustrating PCR-generated bands from individual tumor-Alu-insertion-specific PCR. In panels A to E, the right side shows the normalized number of reads detected for the specific Alu-insertion obtained from Alu-directed sequencing. The left side of panels A to E provides the results of the respective PCR. Primers were designed to amplify the region of the specific Alu insertions; if the insertion is present, a second band of larger size is observed in the DNA from a sample.
Figure 3A:
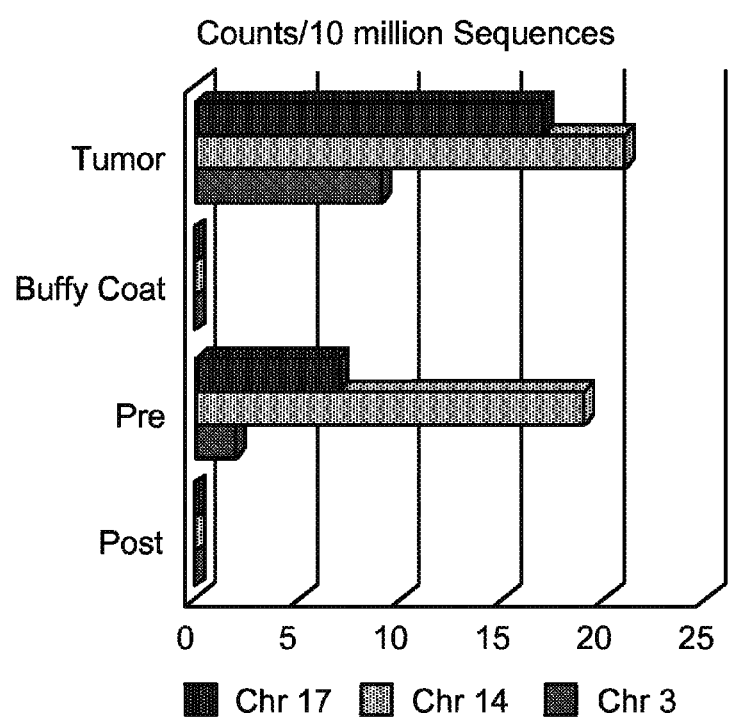
Figure 3B:
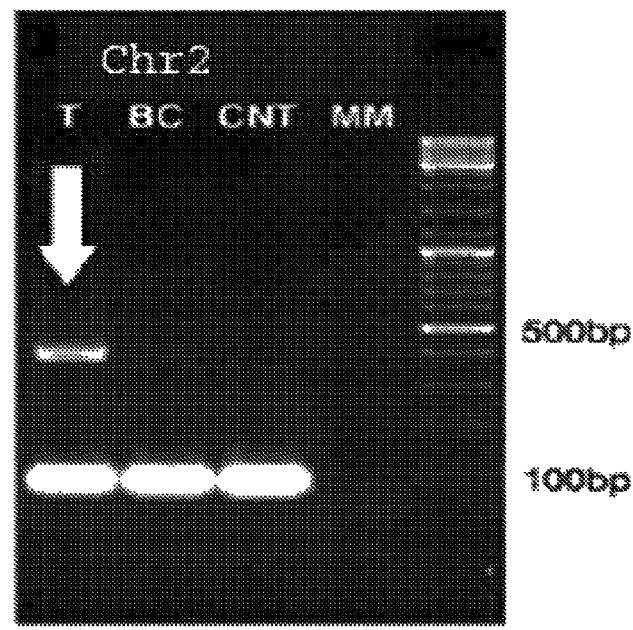
Figure 3B:
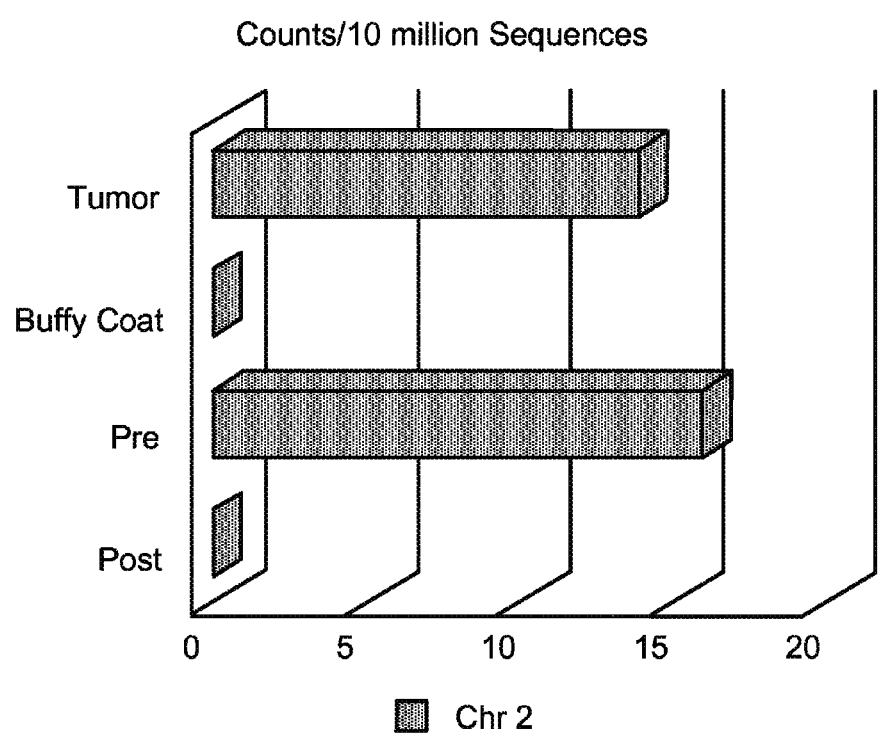
Figure 3C:
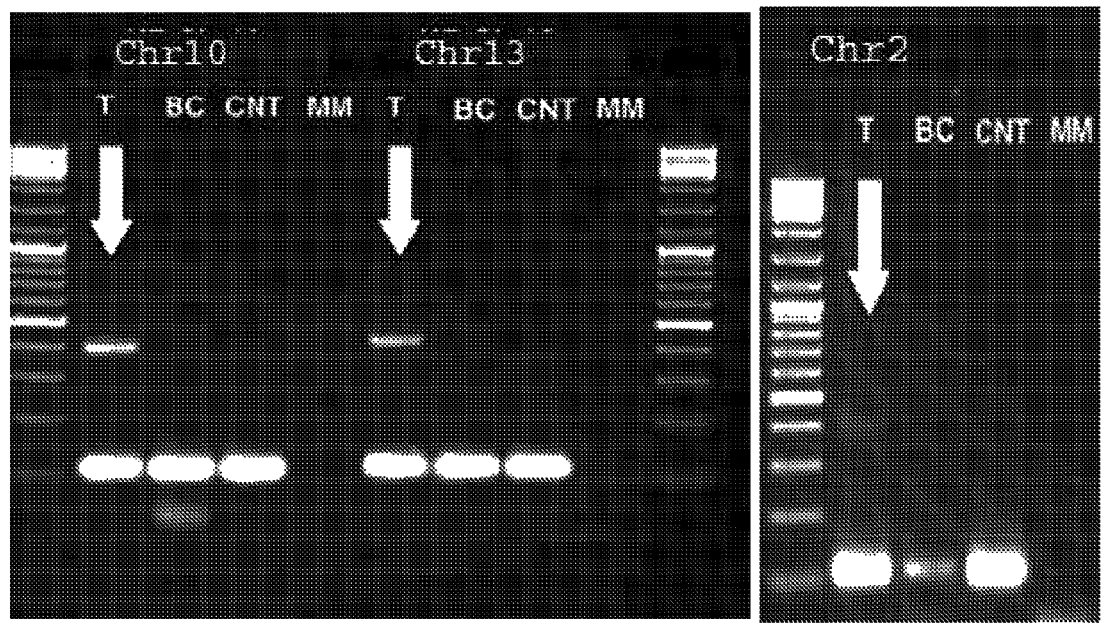
Figure 3C:
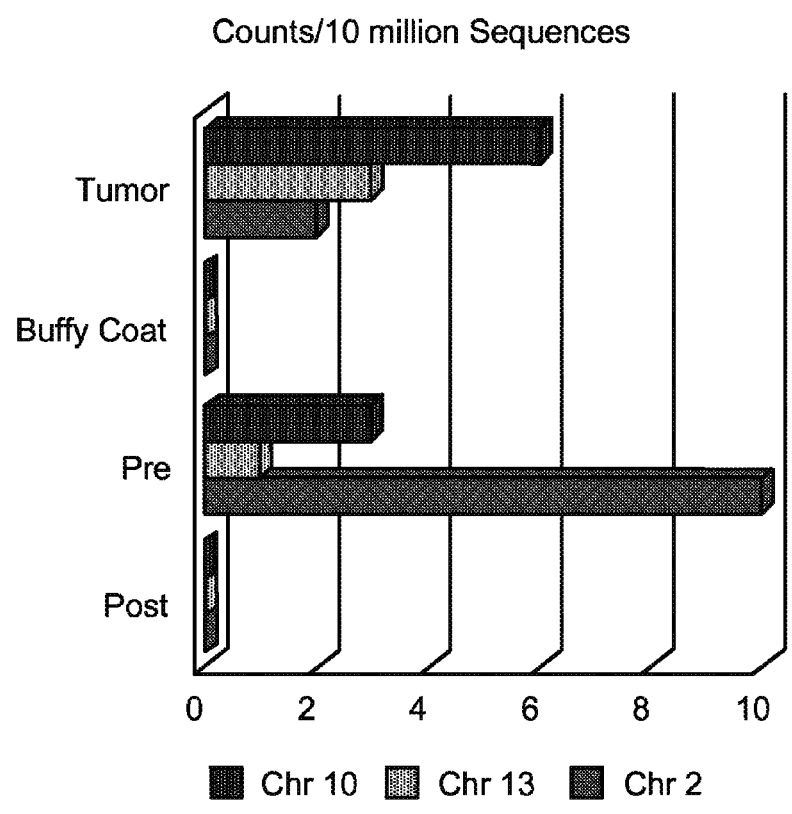
Figure 3D:
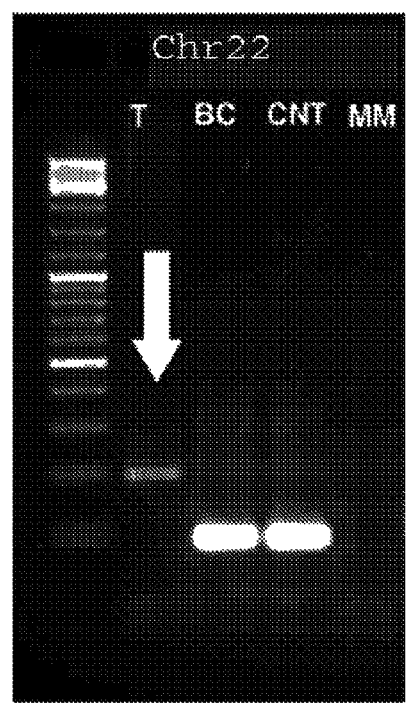
Figure 3D:
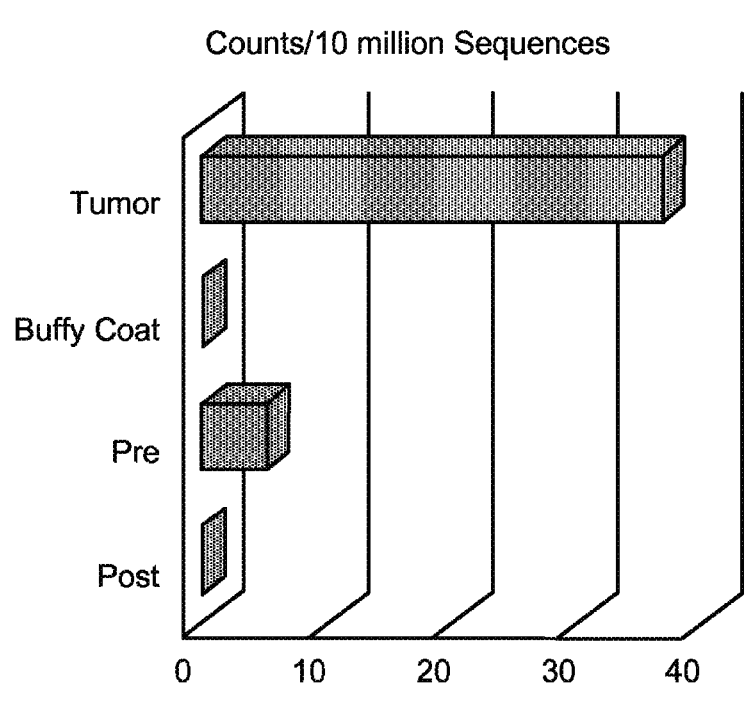
Figure 3E:
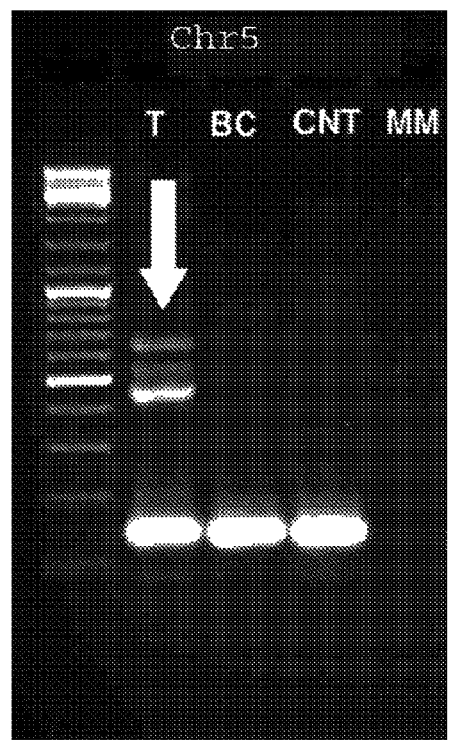
Figure 3E:
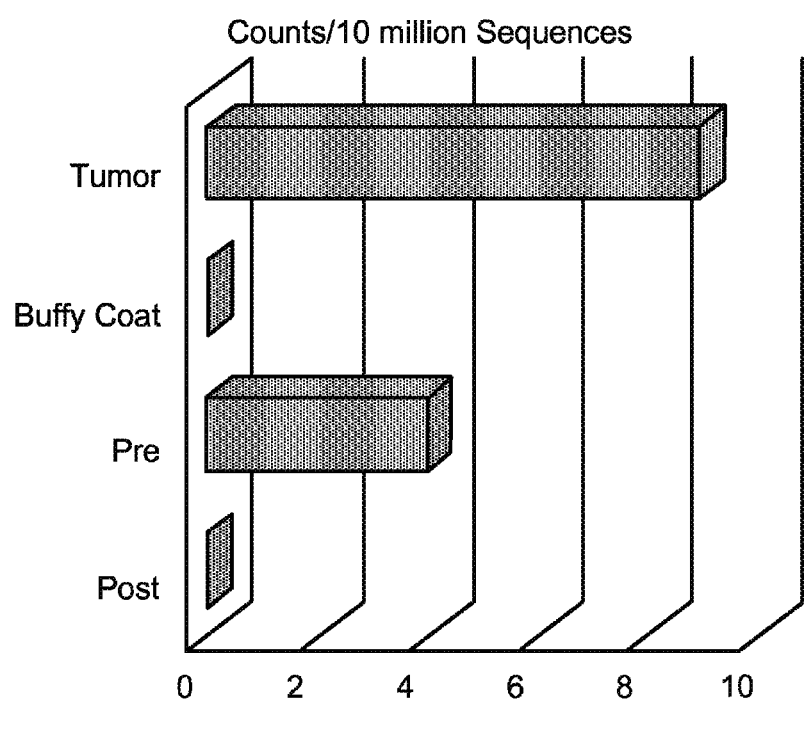
Figure 4A:
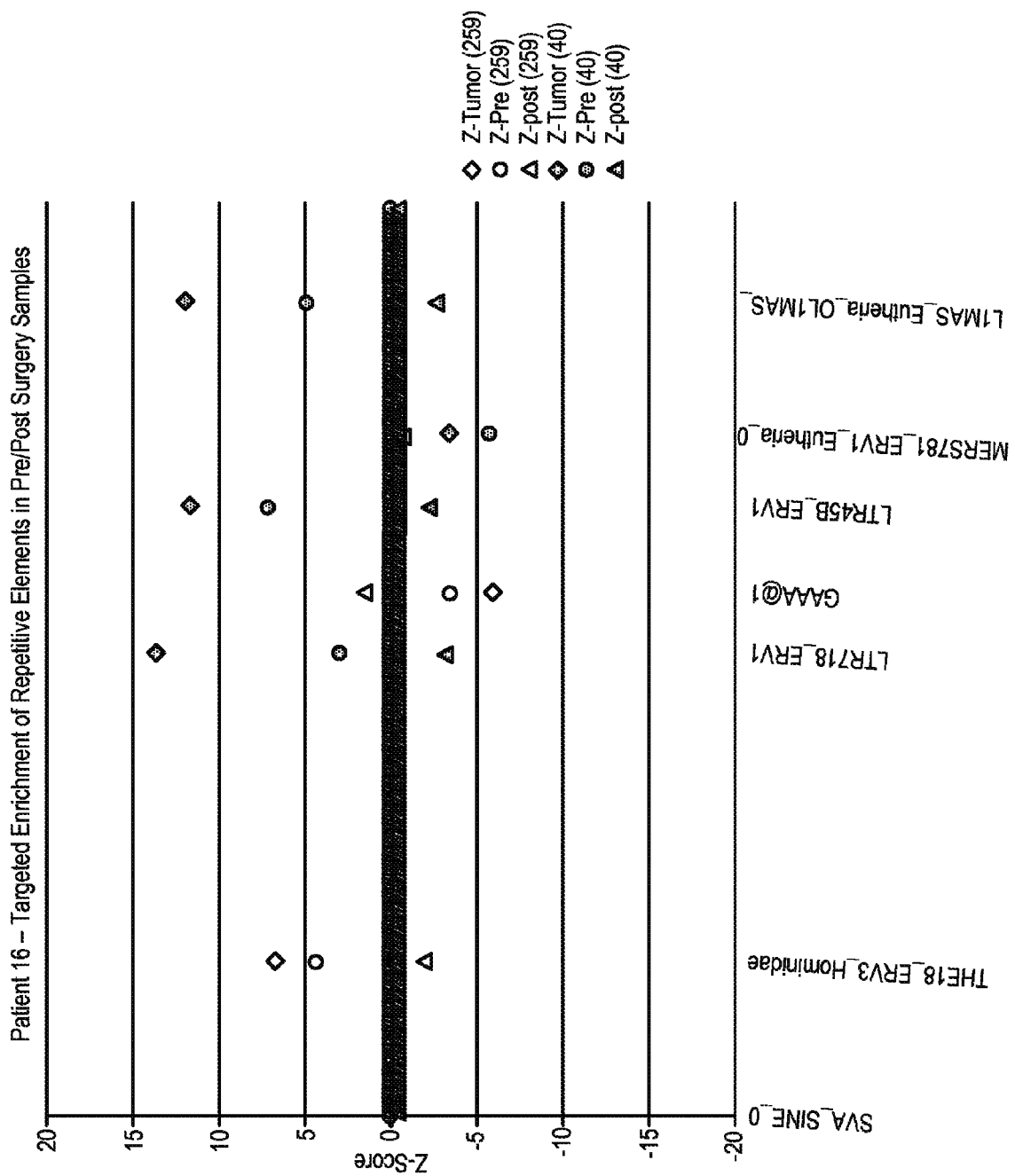
FIG. 4A-E illustrates Z-values for reads of circulating DNA and tumor DNA mapped to known repetitive elements in the human genome, separated for the ALU40 and ALU 259 PCR.
Figure 4B:
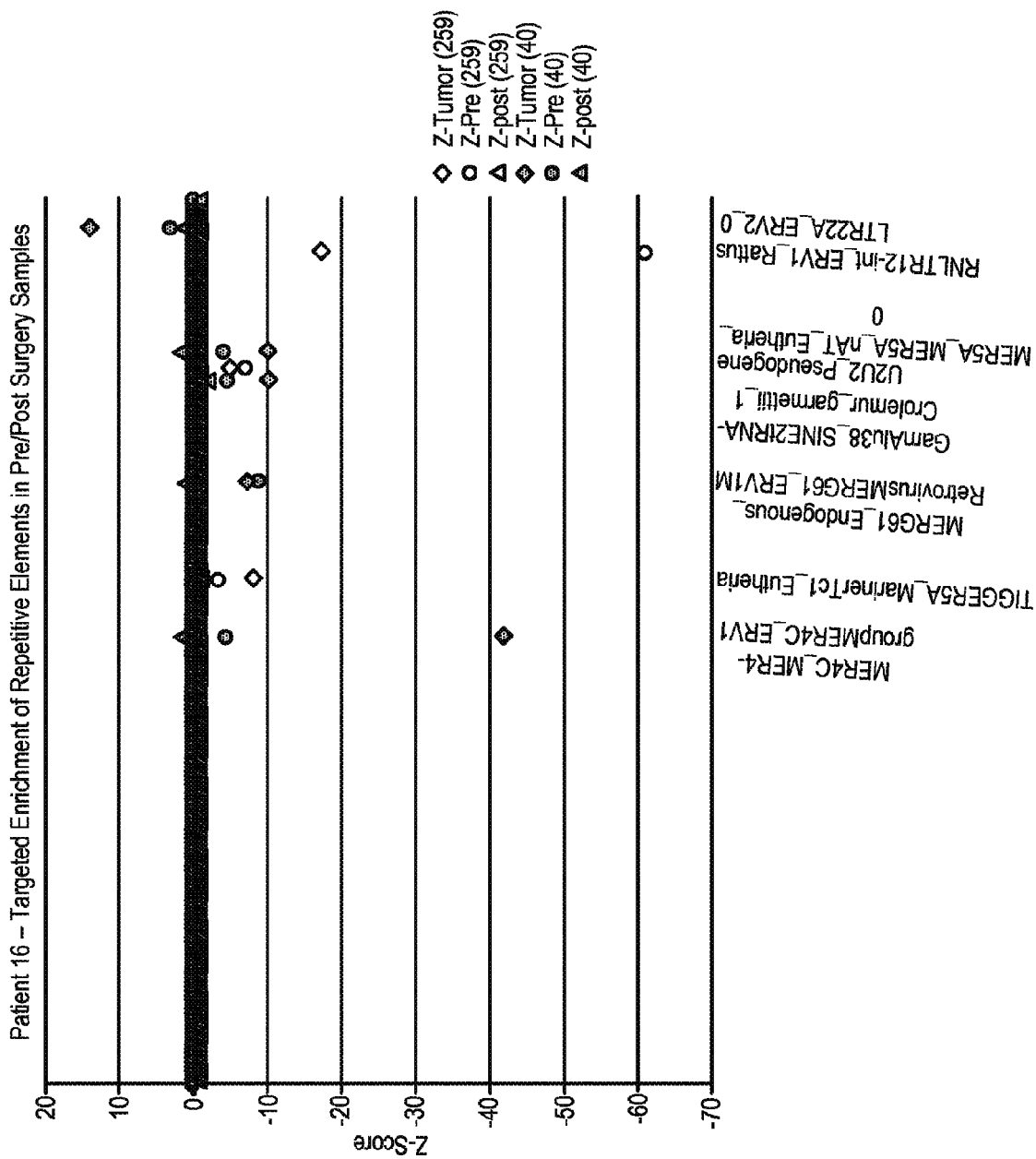
Figure 4C:
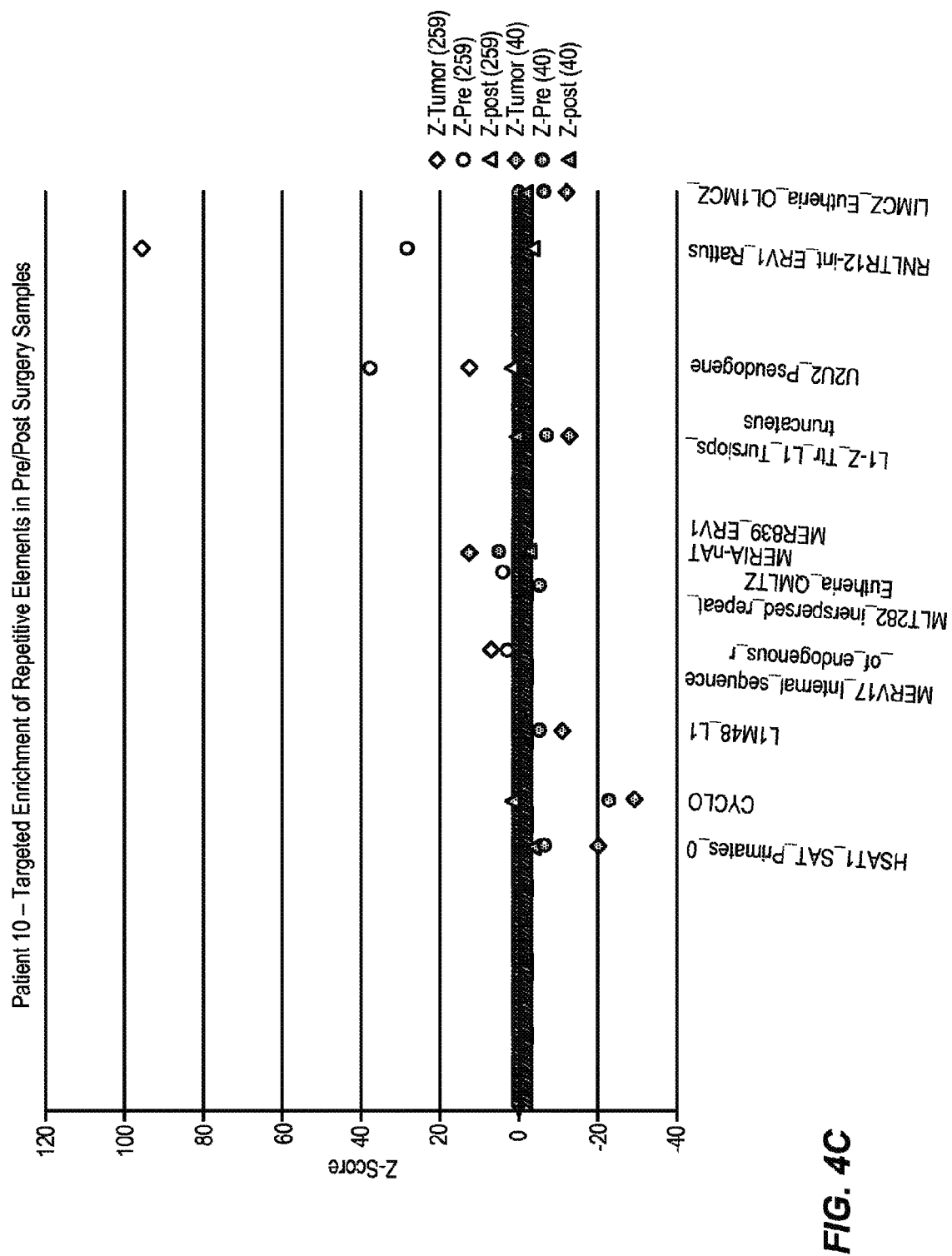
Figure 4D:
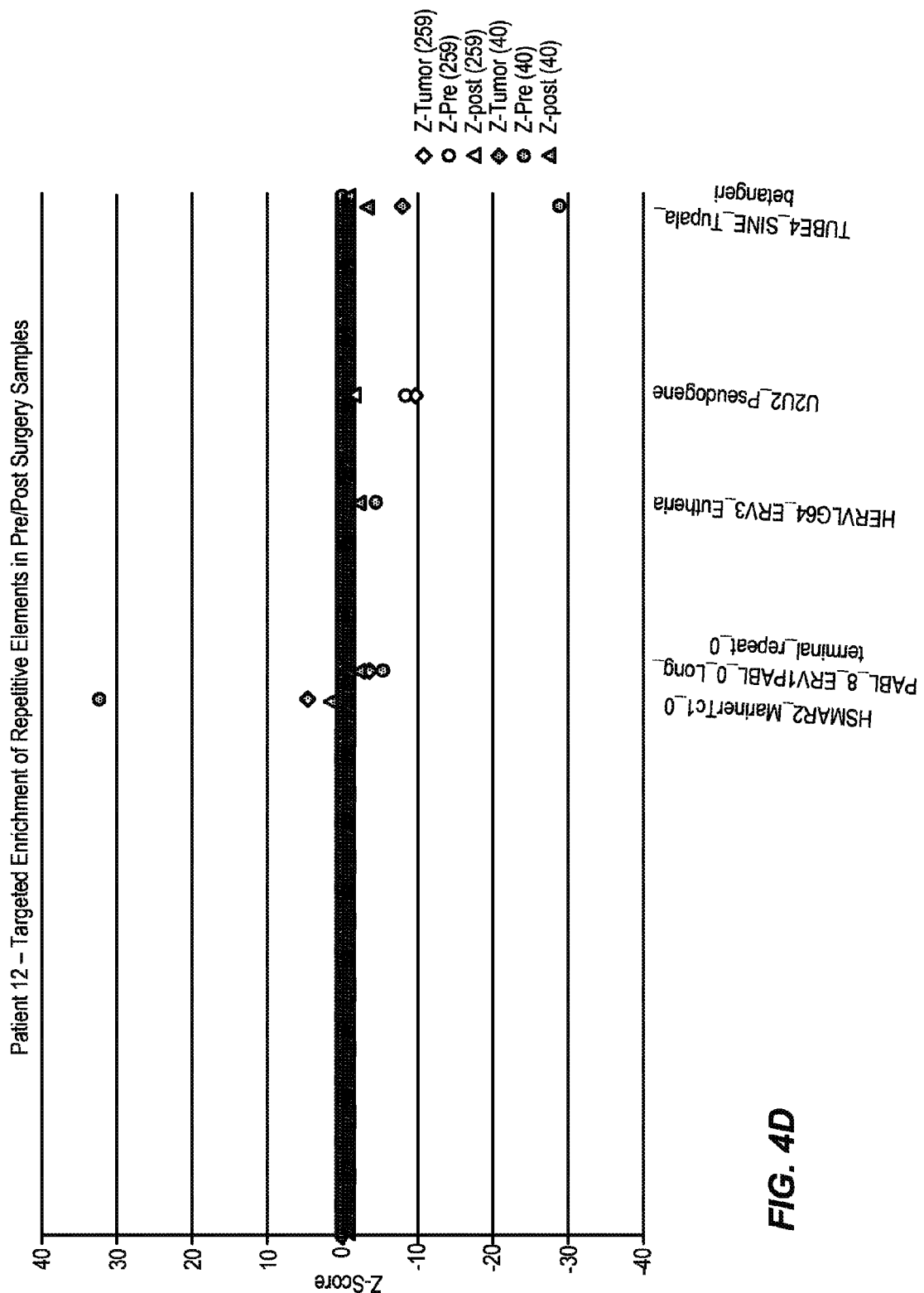
Figure 4E:
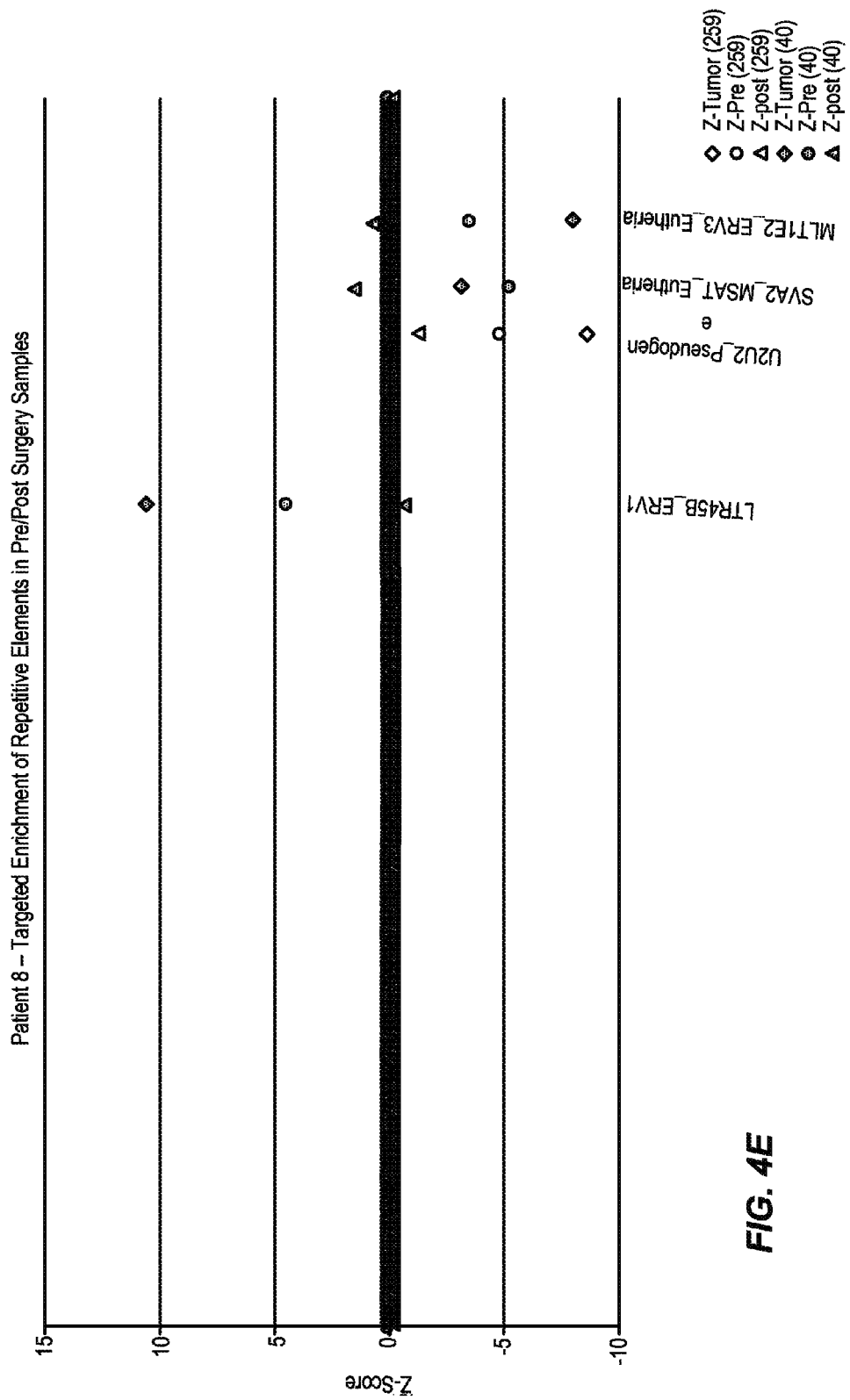

The insertion regions remaining after the filtering procedures, were the putative tumor specific Alu insertion sites. Results are given in Table 1 and are from the algorithm in FIG. 2.

The insertion regions detected in quantitative filtering are given in Table 2. These are the results of the quantitative filtering from selected patients and are used only as an example. This does not represent all regions detected.

PCR Validation Results

Primers spanning some of the putative Alu insertion sites listed in Table 1 were constructed from the human genomic reference genome (HG18, NCBI36, March 2006). Primers were tested on tumor DNA and PBMC DNA of the respective patient. The DNA template used for PCR was in some cases material that was subjected to a pre-amplification using either the Whole-Genome-Amplification 1 Kit (WGA1, Sigma-Aldrich) or the Whole-Genome-Amplification 4 Kit (WGA4, Sigma-Aldrich). A list of primers and the respective template source is provided in Table 3. Agarose gel images of the PCR-amplified products are shown in FIG. 3. FIG. 3 shows the gel analysese for five representative patients, the results of the selection algorithm displayed in FIG. 2. On the right hand side of each panel (A to E) the normalized counts of the specific insertion site is given, which is allocated to ±200 bp in the HG18 database (as described in [0082]). On the left panel, gel images of PCRs that were designed to amplify the particular insertions are shown.

FIG. 4A-E shows Z-values for read of circulating DNA and tumor DNA mapped to known repetitive elements in the human genome, separated for the ALU40 and ALU 259 PCR.

Figure 5A:
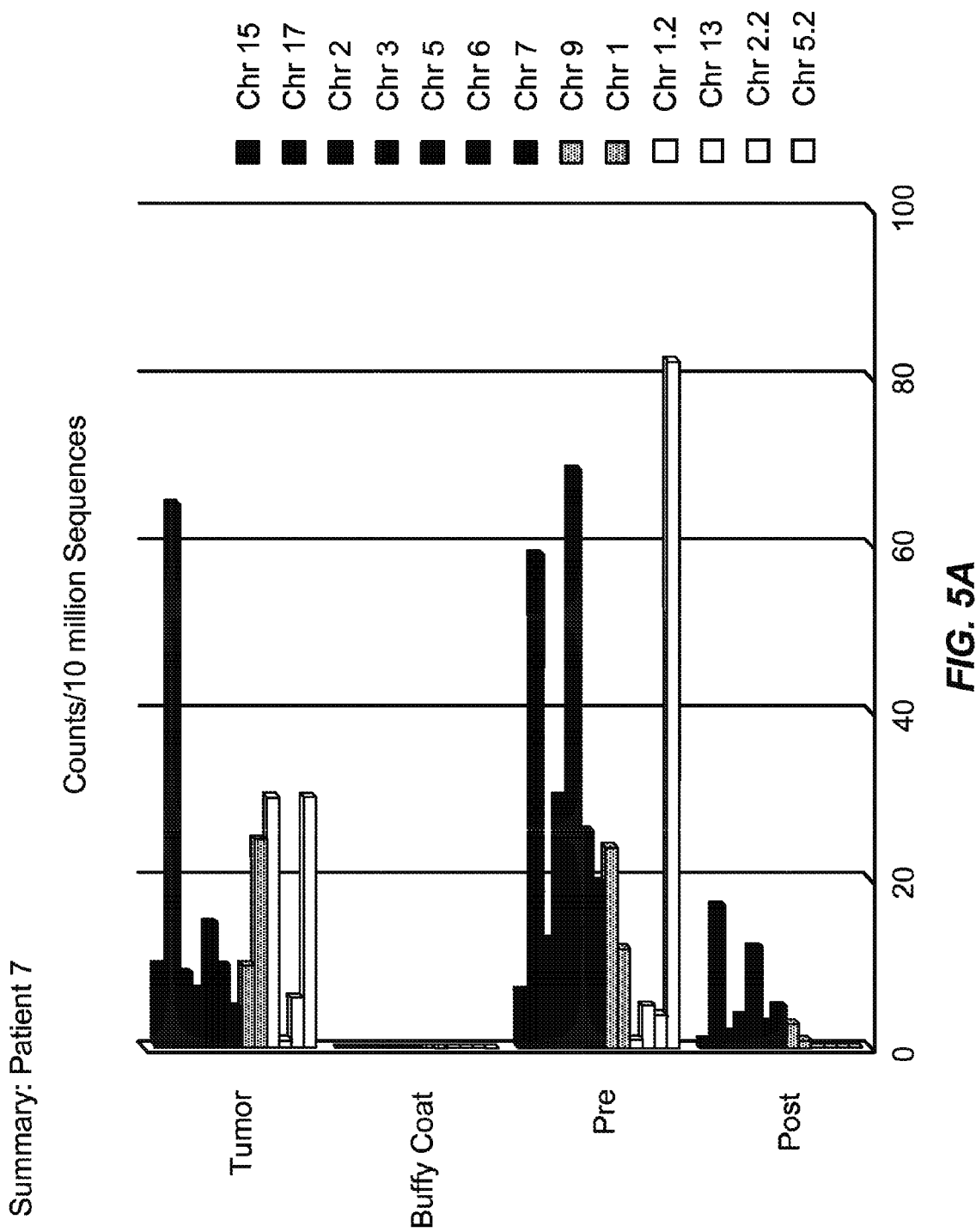
FIG. 5 illustrates the results from two patients showing differential reduction in cell-free DNA biomarkers.
Figure 5B:
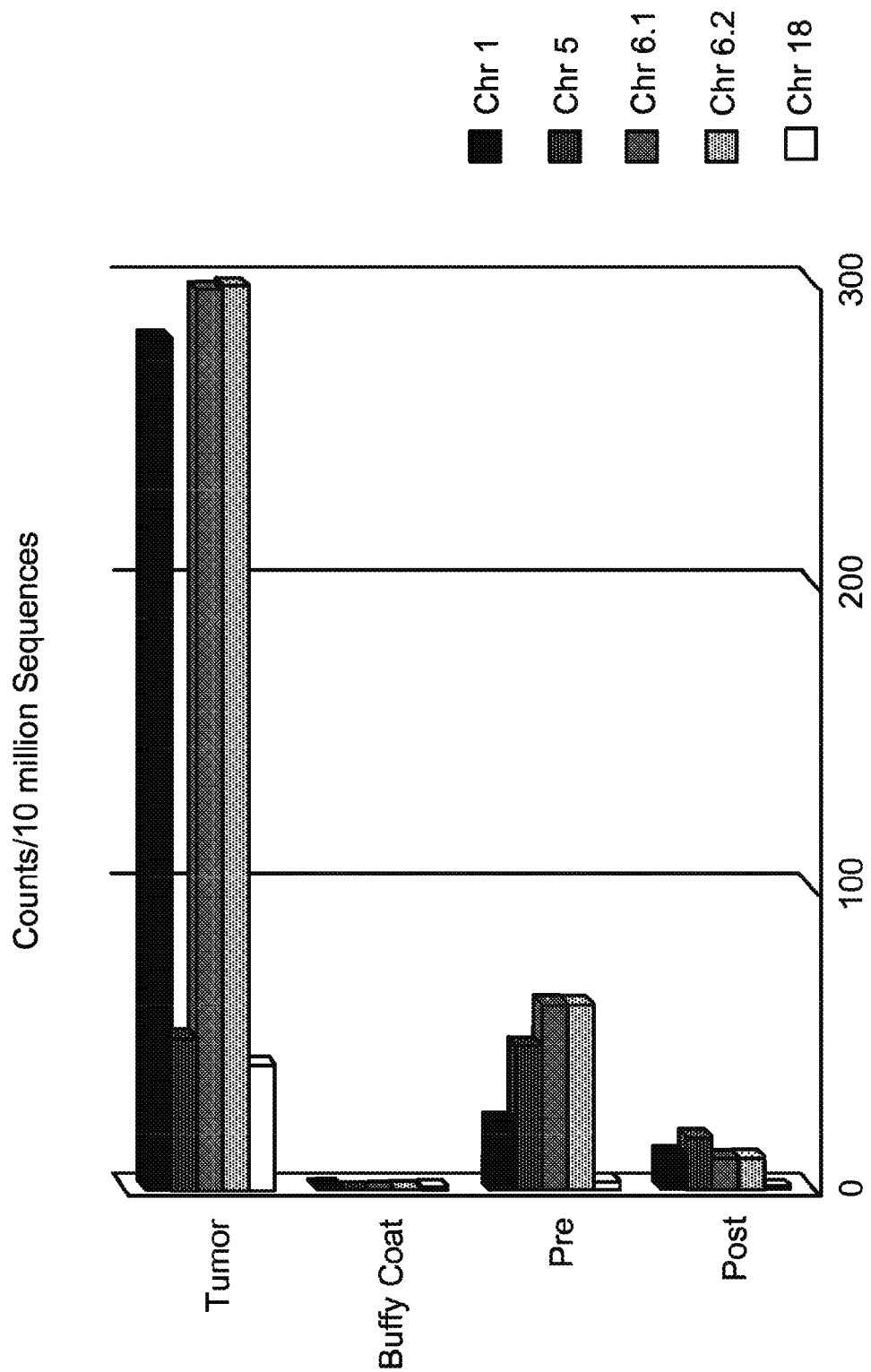

FIG. 5 shows the results for two patients who exhibited differential reduction in cell-free DNA biomarkers. These differential Alu-insertion sites were selected from the quantitative selection procedure illustrated above. Patient 1 in FIG. 5A showed the presence of a tumor specific length polymorphism site located in a unique region on chromosome 18 in the tumor and in the pre-surgical sample. These unique fragments were not detected in either the PBMC or in the post-surgical cell-free DNA sample. Additional length polymorphisms sites in unique regions from chromosomes 1 and 5 and two different unique regions from chromosome 6 were detected in the tumor and pre-surgical cell free DNA sample but not in the PBMC. However, these 4 unique biomarkers could still be detected in the post-surgical sample. Differential reduction in cell-free DNA length polymorphism sites could also be seen in Patient 2 (FIG. 5B). Patient 2 showed complete reduction in post-surgical samples from cell-free DNA from these unique sites on chromosome 1 and chromosome 13, but only a partial reduction in post-surgical cell-free DNA samples in nine other unique differential polymorphisms.

Example 2

This example describes the identification of individualized L1-LINEs biomarkers for colorectal cancer patients.

Library Preparation

Nuclear DNA from (n=12) colorectal cancers and matching white blood cells was extracted using the DNeasy Blood and Tissue Kit (QIAGEN). The extracted DNA was ultrasonically sheared to an average size of 200 bp using a Covaris S220 focused ultrasonicator (Covaris) and AFA microTubes (Covaris). Fragmented DNA (100 ng) was end-repaired, A-tailed and ligated to Illumina sequencing adapters using the NEBNext Ultra Library Preparation Kit (New England Biolabs) according to manufacturer's instructions.

Enrichment

L1 fragment enrichment was conducted using biotinylated L1-specific oligonucleotides (Table 4) and 125 ng library DNA. Hybridization mixtures contained 4 pmol of each L1 probe, 5 µg sheared salmon sperm DNA, 1000 pmol blocking oligos against library specific adapters. After initial denaturation at 950 for 10 min the hybridization was carried out at 47° C. for 72 h. Capture of the biotinylated probes together with the hybridized fragments was conducted using the TargetSeq Hybridization and Wash Kit (Lifetechnologies) according to the manufacturer's instructions. Captured sequences were recovered from the magnetic beads by heat denaturing. The enriched fragments were amplified for 7 cycles of PCR using primers specific for the ligated sequencing adapters.

Sequencing

Paired-end sequencing was conducted on an Illumina HiSeq 2000 producing one 50 bp sequence for each end of the fragments.

Mapping and Filtering

Obtained sequences were mapped against a reference library consisting of all L1 consensus sequences listed in the GIRI RepBase version 18.10. In a next step all read-pairs were selected that had one sequence mapping and one sequence not mapping to the L1 database. The read not mapping to L1 was subsequently mapped against the human reference genome HG19 (CRCh37, February 2009). This second mapping produced the read-pair group "L1-uniqueHG19" containing all pairs that carry a L1 sequence on one side and a unique non-repetitive sequence on the other side.

The unique mapping sequences were filtered by removing all sequences that mapped within a 200 bp window next to an L1 annotated in the reference genome, because those L1 elements are common to the population.

All remaining reads with overlapping mapping positions were grouped into a read-regions. These read-regions were extended by reads that were mapped within 200 bp upstream or downstream.

Next, the read-regions defined in a tumor-sample were compared to the read-region defined for the lymphocyte samples. All tumor read-regions residing within 50 bp upstream or downstream of a lymphocyte read-region were removed, because such reads identify L1 elements that are present in the germline genome and are not somatic de-novo insertions.

All duplicate reads (PCR-duplicates), defined by sharing the exactly same mapping positions were removed from the tumor read-regions.

Finally, all regions containing at least two reads were selected as demarking a somatic de-novo L1 insertion in the tumor genome. Such regions are indicative of a tumor specific L1 insertion, because they (i) contain at least 2 reads of the "L1-uniqueHG19"-class that (ii) are not next to an annotated L1 (population L1) and (iii) are not next to an L1 found in the sequenced lymphocyte genomes (germline L1).

Results:

The enrichment step showed a positive enrichment of 60% (from 44%- to 76%), of reads where at least one of the paired reads could be aligned to the L1-reference sequences. In addition, 1500 reads were identified in which one read aligned uniquely with a non L1 sequence in the human HG19 database and was not annotated to be in the vicinity of a L1 identified in the database.

Figure 6:
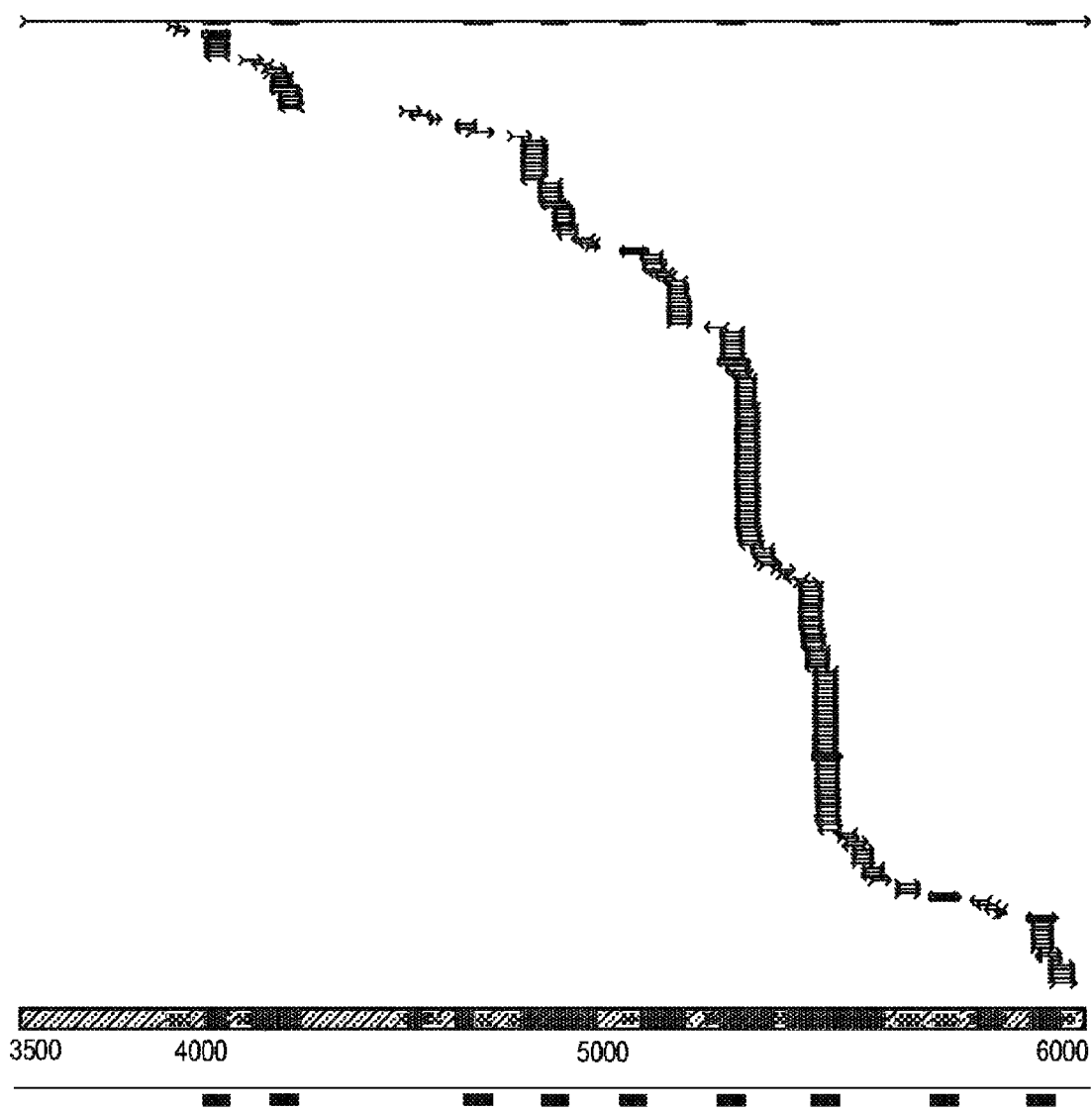
FIG. 6 shows the positioning of L1 reads that have a uniquely mapped pair in reference to the human line L1-HS sequence. Numbers represent the position in L1-HS; black bars at the bottom depict the position of the enrichment probes (Table 4)

When the respective pairs were aligned to the sequence corresponding to the line L1-HS, a fair representation of the regions, used for enrichment (Table 4) could be demonstrated as shown in FIG. 6.

Table 5 shows the chromosomal regions discovered to harbor an L1-HS reinsertion that is only present in the tumor, with position of the reinsertion (HG19) and the position in the L1-HS. When only considering those genomic insertions that are proven by at least two non-identical uniquely mappable read pairs, the distribution of such was variable.

All patents, patent applications, and other published reference materials cited in this specification are hereby incorporated herein by reference in their entirety for their disclosures of the subject matter in whose connection they are cited herein.

TABLE 1

| Patient | Region | Normalized Count Tumor | Normalized count Pre-serum |
|---|---|---|---|
| 1 | chr1: 225668824-225669088 | 3.7 | 0.2 |
| 1 | chr12: 24409844-24409970 | 10.2 | 10.5 |
| 1 | chr13: 57722844-57722974 | 5.9 | 9.1 |
| 1 | chr14: 42810280-42810458 | 8.3 | 12.4 |

TABLE 1-continued

| Patient | Region | Normalized Count Tumor | Normalized count Pre-serum |
|---|---|---|---|
| 1 | chr19: 58728072-58728275 | 8.6 | 5.9 |
| 1 | chr2: 21825477-21825648 | 13.6 | 2.4 |
| 1 | chr2: 176436453-176436623 | 28.1 | 11.1 |
| 1 | chr3: 16771014-16771238 | 7.7 | 5.9 |
| 1 | chr8: 143078294-143078459 | 21.9 | 20.9 |
| 2 | chr1: 84210120-84210310 | 6.0 | 53.5 |
| 2 | chr12: 7515352-7515583 | 57.4 | 16.0 |
| 2 | chr12: 125812263-125812481 | 21.8 | 38.6 |
| 2 | chr4: 180935360-180935572 | 18.4 | 17.8 |
| 2 | chr9: 112366790-112366988 | 10.9 | 43.7 |
| 3 | chr1: 1639582-1639655 | 21.2 | 4.6 |
| 3 | chr1: 4188245-4188411 | 11.8 | 17.1 |
| 3 | chr1: 8400021-8400166 | 2.5 | 3.8 |
| 3 | chr15: 95386890-95386999 | 2.5 | 12.7 |
| 3 | chr3: 156523259-156523435 | 8.3 | 10.1 |
| 4 | chr1: 42744531-42744674 | 21.3 | 8.3 |
| 4 | chr1: 75476043-75476177 | 5.3 | 8.6 |
| 4 | chr10: 42569993-42570152 | 1.2 | 10.1 |
| 4 | chr11: 37501169-37501278 | 24.2 | 5.4 |
| 4 | chr12: 30311840-30311991 | 12.1 | 0.9 |
| 4 | chr14: 83527163-83527342 | 44.6 | 9.7 |
| 4 | chr16: 69712044-69712214 | 13.0 | 13.3 |
| 4 | chr2: 195725724-195725913 | 31.6 | 9.0 |
| 4 | chr2: 212553961-212554174 | 44.3 | 110.0 |
| 4 | chr3: 105796302-105796413 | 1.8 | 0.9 |
| 4 | chr4: 81355631-81355798 | 33.9 | 7.4 |
| 4 | chr4: 110357587-110357711 | 1.8 | 4.3 |
| 4 | chr5: 91066686-91066828 | 57.3 | 32.9 |
| 4 | chr7: 54903338-54903491 | 1.5 | 2.3 |
| 4 | chrX: 5791690-5791836 | 61.7 | 16.7 |
| 5 | chr1: 43981427-43981622 | 1.3 | 4.5 |
| 5 | chr13: 34083152-34083273 | 1.3 | 5.6 |
| 5 | chr2: 159718375-159718655 | 14.3 | 16.2 |
| 5 | chr21: 9733224-9733404 | 10.2 | 9.2 |
| 6 | chr2: 189381538-189381696 | 7.4 | 12.1 |
| 7 | chr1: 179854863-179855092 | 29.9 | 1.2 |
| 7 | chr13: 106742744-106742969 | 1.1 | 5.2 |
| 7 | chr2: 185709935-185710118 | 5.8 | 3.7 |
| 7 | chr5: 42661495-42661726 | 30.6 | 81.9 |
| 8 | chr1: 48745030-48745205 | 3.8 | 8.1 |
| 8 | chr10: 82375975-82376135 | 2.5 | 3.5 |
| 8 | chr15: 22308807-22308935 | 3.6 | 0.7 |
| 8 | chr2: 186829894-186830068 | 10.4 | 2.4 |
| 8 | chr4: 126197098-126197290 | 3.0 | 2.1 |
| 8 | chr4: 167680779-167680958 | 2.7 | 1.2 |
| 8 | chr5: 22454057-22454245 | 7.7 | 17.5 |
| 8 | chr5: 39974140-39974294 | 8.8 | 4.3 |
| 8 | chr5: 100087972-100088160 | 14.0 | 0.3 |
| 8 | chr7: 13615684-13615825 | 3.8 | 8.0 |
| 8 | chr7: 53325677-53325895 | 4.7 | 1.0 |
| 8 | chr7: 70306861-70307058 | 11.5 | 10.0 |
| 8 | chr9: 104533909-104534105 | 19.5 | 1.6 |
| 8 | chr9: 104533909-104534079 | 19.2 | 1.6 |
| 8 | chrX: 93248625-93248818 | 6.6 | 4.5 |
| 10 | chr1: 243242339-243242484 | 29.3 | 6.4 |
| 10 | chr10: 131942955-131943134 | 5.6 | 3.4 |
| 10 | chr13: 90100261-90100403 | 2.5 | 1.1 |
| 10 | chr16: 34560792-34560945 | 7.6 | 12.6 |
| 10 | chr2: 196460079-196460192 | 2.0 | 9.6 |
| 10 | chr3: 39551193-39551311 | 3.4 | 4.9 |
| 10 | chr5: 37290632-37290828 | 5.1 | 9.4 |
| 10 | chr6: 88754697-88754859 | 14.6 | 8.1 |
| 10 | chr7: 66008688-66008803 | 1.1 | 1.5 |
| 10 | chr7: 79070027-79070178 | 7.3 | 1.1 |
| 10 | chr9: 101889046-101889180 | 11.0 | 4.1 |
| 20 | chrX: 118996698-118996791 | 2.0 | 0.9 |
| 12 | chr1: 34015349-34015535 | 12.5 | 14.2 |
| 12 | chr12: 75835772-75835995 | 79.1 | 8.2 |
| 12 | chr22: 33566325-33566494 | 37.4 | 5.2 |
| 12 | chr22: 33566363-33566494 | 37.0 | 5.2 |
| 13 | chr1: 1639596-1639647 | 4.7 | 0.5 |
| 13 | chr1: 85528031-85528246 | 54.4 | 34.1 |
| 13 | chr12: 24409804-24409963 | 24.0 | 4.8 |
| 13 | chr12: 30311833-30312024 | 4.1 | 14.0 |
| 13 | chr13: 31133521-31133722 | 29.4 | 8.7 |
| 13 | chr13: 45993298-45993556 | 1.4 | 1.6 |
| 13 | chr15: 65399680-65399845 | 2.4 | 1.6 |
| 13 | chr7: 34286418-34286606 | 7.8 | 2.6 |
| 15 | chr18: 26245362-26245606 | 41.4 | 2.8 |
| 16 | chr1: 104871623-104871854 | 52.7 | 15.7 |
| 16 | chr1: 160497612-160497806 | 50.6 | 29.6 |
| 16 | chr1: 211908140-211908291 | 52.1 | 1.1 |
| 16 | chr1: 224008418-224008652 | 1.5 | 0.8 |
| 16 | chr10: 71673503-71673740 | 10.4 | 4.7 |
| 16 | chr10: 78166563-78166804 | 10.4 | 11.9 |
| 16 | chr11: 5834094-5834295 | 5.5 | 4.4 |
| 16 | chr12: 79004761-79004964 | 35.0 | 36.0 |
| 16 | chr12: 84141777-84141935 | 8.9 | 2.1 |
| 16 | chr13: 88382677-88382881 | 11.7 | 16.7 |
| 16 | chr14: 38578161-38578387 | 20.8 | 18.8 |
| 16 | chr14: 60568102-60568269 | 7.4 | 3.0 |
| 16 | chr15: 21681844-21682154 | 36.2 | 16.5 |
| 16 | chr17: 27923192-27923393 | 17.5 | 7.4 |
| 16 | chr18: 72971240-72971441 | 49.7 | 8.5 |
| 16 | chr19: 22756096-22756273 | 19.3 | 2.8 |
| 16 | chr19: 35541770-35541973 | 3.4 | 3.0 |
| 16 | chr19: 36660194-36660423 | 22.1 | 3.6 |
| 16 | chr2: 35143314-35143471 | 2.5 | 0.4 |
| 16 | chr2: 84631424-84631656 | 86.5 | 13.3 |
| 16 | chr2: 106026857-106027104 | 16.3 | 4.7 |
| 16 | chr2: 137936742-137936888 | 17.8 | 10.2 |
| 16 | chr2: 167109411-167109623 | 7.1 | 12.7 |
| 16 | chr2: 216279158-216279366 | 12.0 | 47.2 |
| 16 | chr2: 216279195-216279366 | 5.8 | 46.6 |
| 16 | chr2: 229962184-229962546 | 26.1 | 29.4 |
| 16 | chr2: 236356980-236357204 | 8.9 | 8.7 |
| 16 | chr20: 8134573-8134740 | 3.7 | 5.9 |
| 16 | chr20: 51803208-51803323 | 3.7 | 20.5 |
| 16 | chr3: 74888046-74888192 | 8.9 | 2.1 |
| 16 | chr3: 128978403-128978648 | 77.6 | 66.9 |
| 16 | chr3: 136882961-136883146 | 11.0 | 4.9 |
| 16 | chr3: 167384636-167384854 | 11.3 | 35.2 |
| 16 | chr4: 12257674-12257901 | 8.9 | 1.1 |
| 16 | chr4: 12257674-12257899 | 8.3 | 1.1 |
| 16 | chr4: 18081638-18081865 | 7.4 | 12.1 |
| 16 | chr4: 129081215-129081401 | 20.5 | 9.1 |
| 16 | chr5: 1493804-1493894 | 4.0 | 1.9 |
| 16 | chr5: 10475757-10475924 | 46.6 | 13.1 |
| 16 | chr5: 59655387-59655550 | 2.1 | 4.2 |
| 16 | chr5: 95356487-95356755 | 54.6 | 10.8 |
| 16 | chr5: 103230987-103231140 | 6.1 | 4.7 |
| 16 | chr5: 129721638-129721818 | 13.8 | 3.0 |
| 16 | chr5: 168710716-168710926 | 23.9 | 28.4 |
| 16 | chr6: 5293628-5293816 | 3.1 | 8.3 |
| 16 | chr6: 110557420-110557574 | 37.7 | 47.9 |
| 16 | chr6: 119435653-119435855 | 15.0 | 7.6 |
| 16 | chr6: 119435653-119435819 | 7.1 | 7.6 |
| 16 | chr6: 123599662-123599856 | 14.4 | 3.0 |
| 16 | chr7: 55554702-55554866 | 13.8 | 15.2 |
| 16 | chr7: 61259199-61259372 | 28.8 | 99.1 |
| 16 | chr7: 95550567-95550810 | 22.7 | 3.0 |
| 16 | chr7: 102304106-102304342 | 22.7 | 20.8 |
| 16 | chr7: 141355925-141356108 | 4.6 | 3.4 |
| 16 | chr8: 59661474-59661654 | 37.4 | 101.9 |
| 16 | chr8: 82587476-82587688 | 64.1 | 25.0 |
| 16 | chr9: 26167010-26167139 | 10.1 | 17.4 |
| 16 | chr9: 26167025-26167139 | 5.8 | 17.4 |
| 16 | chr9: 107120758-107120970 | 6.7 | 4.2 |
| 16 | chrX: 35176776-35176937 | 13.2 | 17.6 |
| 16 | chrX: 93248594-93248891 | 4.6 | 13.1 |
| 17 | chr1: 4188229-4188422 | 61.0 | 19.6 |
| 17 | chr12: 79004801-79004893 | 4.7 | 4.1 |
| 17 | chr16: 74212566-74212745 | 71.8 | 10.3 |
| 17 | chr4: 41778429-41778642 | 81.4 | 65.0 |
| 17 | chr5: 18955266-18955494 | 9.3 | 4.3 |
| 17 | chr6: 53275296-53275532 | 9.6 | 2.1 |
| 17 | chr7: 116753272-116753466 | 14.3 | 3.2 |
| 17 | chr8: 3034589-3034766 | 2.3 | 10.7 |
| 17 | chr8: 17987284-17987515 | 18.1 | 3.9 |
| 17 | chrX: 86482191-86482398 | 7.9 | 1.8 |

TABLE 2

| Patient | Region | Normalized Count Tumor | Normlized count PBMC | Normalized count Pre-serum | Normalized count post-serum |
|---|---|---|---|---|---|
| \multicolumn{6}{c}{4xPBMC < Tu & 2xPost < Pre} | | | | | |
| 5 | chr4: 180935376-180935564 | 23.23367202 | 0 | 23.96991786 | 6.13522487 |
| 6 | chr10: 113995673-113995829 | 1.598943214 | | 37.17017141 | 11.1092118 |
| 6 | chr14: 38230428-38230622 | 32.9382302 | 0.24/0.88 | 123.1571679 | 44.8408184 |
| 6 | chr14: 87657285-87657463 | 11.1926025 | | 24.53231313 | 6.46354139 |
| 6 | chr9: 14867350-14867546 | 8.634293354 | | 58.48106969 | 10.9072261 |
| 6 | chr9: 89135762-89135898 | 12.79154571 | | 93.9166331 | 29.2879219 |
| 9 | chr18: 20355821-20355995 | 15.67390694 | | 35.50994404 | 13.0295755 |
| 9 | chr3: 6611827-6611963 | 4.528017561 | | 197.5921426 | 41.5875492 |
| 9 | chr5: 35456477-35456658 | 4.179708518 | | 35.50994404 | 7.31798076 |
| 9 | chr8: 130024849-130025036 | 14.62897981 | | 101.5192265 | 33.0201571 |
| 9 | chr8: 132446963-132447159 | 20.55023355 | | 120.9080917 | 27.8440243 |
| 14 | chr10: 72275346-72275501 | 22.84380142 | 0.13575 | 23.52753959 | 15.614494 |
| 15 | chr1: 69863579-69863750 | 282.3202084 | 1.033791 | 23.99745741 | 12.1546129 |
| 15 | chr5: 55547575-55547662 | 49.98456148 | | 47.58817825 | 18.0068339 |
| 15 | chr6: 120421873-120421996 | 298.9817289 | | 61.82395807 | 11.0291858 |
| \multicolumn{6}{c}{4xPBMC < Tu & 4xPost < Pre} | | | | | |
| 6 | chr9: 14867350-14867546 | 8.634293354 | 0 | 58.48106969 | 10.9072261 |
| 7 | chr1: 212977517-212977735 | 25.15932599 | | 11.67053095 | 1.28400063 |
| 7 | chr15: 84025866-84026064 | 9.844953648 | | 7.141668192 | 1.07000053 |
| 7 | chr17: 32996024-32996267 | 64.9037685 | | 59.39777691 | 17.3340085 |
| 7 | chr2: 115550251-115550458 | 8.751069909 | | 12.88984015 | 2.14000105 |
| 7 | chr3: 164908141-164908357 | 7.292558258 | | 29.61179494 | 4.49240221 |
| 7 | chr5: 98633992-98634189 | 15.31437234 | | 69.32643757 | 11.7700058 |
| 7 | chr6: 128375720-128375918 | 9.844953648 | | 25.60549327 | 3.21000158 |
| 7 | chr7: 53325693-53325892 | 4.740162868 | | 19.85732131 | 5.35000263 |
| 7 | chr9: 102742619-102742818 | 9.844953648 | | 24.21199704 | 3.21000158 |
| 11 | chr15: 25852912-25853071 | 11.05459787 | 0 | 29.29110425 | 5.24337296 |
| 12 | chr12: 95944094-95944285 | 22.97521656 | | 44.16152383 | 5.5623034 |
| 12 | chr17: 47404627-47404853 | 9.345850802 | | 58.94864041 | 20.0242922 |
| 15 | chr6: 120421873-120421996 | 298.9817289 | 3.205797 | 61.82395807 | 11.0291858 |
| \multicolumn{6}{c}{4xPBMC < Tu & 10xPost < Pre} | | | | | |
| 7 | chr1: 212977517-212977735 | 25.15932599 | | 11.67053095 | 1.28400063 |
| 12 | chr12: 95944094-95944285 | 22.97521656 | | 44.16152383 | 5.5623034 |

TABLE 3

| Primer Name | Primer Sequence | Template source tumor DNA | Template source PBMC DNA |
|---|---|---|---|
| 16-chr17: 27923338-27923393.F | TTGTATTACTTCT TGACCACATTAAA | WGA1 | WGA1 |
| 16-chr17: 27923338-27923393.R | CGAGGGGGAGTAA AAGTGCT | WGA1 | WGA1 |
| 16-chr14: 38578285-38578387.F | AAATGCACCTCTT CTCTCCA | WGA1 | WGA1 |
| 16-chr14: 38578285-38578387.R | ATGCTGAGTTTTG GACTCAA | WGA1 | WGA1 |
| 16-chr3: 74888046-74888097.F | AAACATCTTTAAT CCCCAGCA | WGA1 | WGA1 |
| 16-chr3: 74888046-74888097.R | TTCCTTAGATCAG GCACATTT | WGA1 | WGA1 |
| 5-chr2: 159718375-159718655.F | GCCACAGGTCTTT GAAGAGG | WGA1 | WGA1 |
| 5-chr2: 159718375-159718655.R | GGAACCTGCACAC CCTGTAT | WGA1 | WGA1 |
| 10-chr13: 90100261-90100403.F | CAAATCTCAAGAG TTTATGATGTACC | WGA1 | WGA4 |
| 10-chr13: 90100261-90100403.R | CCTAGAGAGATTG GGGGCTAA | WGA1 | WGA4 |
| 10-chr2: 196460079-196460192.F | GCACATTTTAAAA AGCTTGCAG | WGA1 | WGA4 |
| 10-chr2: 196460079-196460192.R | CGAATTTTCTATG TAACTGAAACA | WGA1 | WGA4 |
| 10-chr10: 131942955-131943134.F | GAGAGGGCTTCCT GAGATACC | WGA1 | WGA4 |
| 10-chr10: 131942955-131943134.R | TCCACCATCGGAG AATAAGG | WGA1 | WGA4 |
| 12-chr22: 33566363-33566494.F | AGCCACATGACCG CCTTCT | WGA1 | WGA1 |
| 12-chr22: 33566363-33566494.R | TGTTTGACCAGGA CCCTGAC | WGA1 | WGA1 |

TABLE 4

| Name | Sequence |
| --- | --- |
| Probe4000<br>SEQ ID NO: 9 | CTGGCACAAGACAGGGATGCCCTCTCTCACCGCTCC<br>TATTCAACATAGTGTTGGAAGTTC |
| Probe4117<br>SEQ ID NO: 10 | CCCCATCGTCTCAGCCCAAAATCTCCTTAAGCTGAT<br>AAGCAACTTCAGCAAAGTCTCAGG |
| Probe4500<br>SEQ ID NO: 11 | CTGGAGGCATCACACTACCTGACTTCAAACTATACT<br>ACAAGGCTACAGTAACCAAAACAG |
| Probe4759<br>SEQ ID NO: 12 | GCAATGGGGAAAGGATTCCCTATTTAATAAATGGTG<br>CTGGGAAAACTGGCTAGCCATATG |
| Probe5000<br>SEQ ID NO: 13 | GGCGTGGGCAAGGACTTCATGTCCAAAACACCAAAA<br>GCAATGGCAACAAAAGCCAAAATT |

TABLE 4-continued

| Name | Sequence |
| --- | --- |
| Probe5182<br>SEQ ID NO: 14 | AAACAACCCCATCAAAAAGTGGGCGAAGGACATGAA<br>CAGACACTTCTCAAAAGAAGACAT |
| Probe5500<br>SEQ ID NO: 15 | CACTGTTGGTGGGACTGTAAACTAGTTCAACCATTG<br>TGGAAGTCAGTGTGGCGATTCCTC |
| Probe5699<br>SEQ ID NO: 16 | GATGAGTTCATATCCTTTGTAGGGACATGGATGAAA<br>TTGGAAACCATCATTCTCAGTAAAC |
| Probe6000<br>SEQ ID NO: 17 | GGGTGCAGCGCACCAGCATGGCACATGTATACATAT<br>GTAACTAACCTGCACAATGTGCAC |

TABLE 5

| Tumor | Region | Reads in region | Mapping positions L1 | Mapping positions HG19 |
| --- | --- | --- | --- | --- |
| 344 | chr22: 37806031-37806149 | 3 | 5266, 5892, 5892 | chr22: 37806100(−), chr22: 37806033(+), chr22: 37806032(+) |
| 344 | chr20: 62902155-62902421 | 3 | 4843, 5199, 5199 | chr20: 62902257(+), chr20: 62902156(+), chr20: 62902372(+) |
| 344 | chr12: 16502625-16502869 | 2 | 5936, 5826 | chr12: 16502810(−), chr12: 16502820(−) |
| 318 | chr3: 76827019-76827093 | 4 | 5609, 5628, 5647, 5557 | chr3: 76827020(+), chr3: 76827022(+), chr3: 76827025(+), chr3: 76827044(+) |
| 317 | chr13: 42440357-42440719 | 3 | 5349, 5804, 5970 | chr13: 42440358(+), chr13: 42440567(−), chr13: 42440670(−) |
| 315 | chr13: 108859513-108859718 | 2 | 4765, 4801 | chr13: 108859662(+), chr13: 108859669(+) |
| 119 | chr5: 88629449-88629608 | 2 | 5956, 5193 | chr5: 88629450(+), chr5: 88629499(−) |
| 119 | chr7: 129888058-129888246 | 3 | 5675, 5650, 5659 | chr7: 129888059(+), chr7: 129888063(+), chr7: 129888085(+) |
| 119 | chr15: 58669421-58669609 | 3 | 5352, 5810, 5810 | chr15: 58669422(+), chr15: 58669558(−), chr15: 58669559(−) |
| 119 | chrX: 38768199-38768309 | 3 | 3903, 3857, 3847 | chrX: 38768200(+), chrX: 38768246(+), chrX: 38768260(+) |

What is claimed is:

1. A method of identifying a repetitive element insertion region that is present in a tumor, but not peripheral blood mononuclear cells (PBMCs) for a patient having a tumor who is to undergo a therapy to treat the tumor, the method comprising:
   (a) obtaining nucleic acid samples comprising DNA from the patient from each of the following sources: PBMCs, the tumor, and pre-therapy cell-free nucleic acids, which nucleic acids are obtained prior to the therapy;
   (b) preparing a library of DNA fragments from each of the nucleic acid samples;
   (c) performing sequencing reactions to sequence the DNA fragments in the libraries to identify DNA fragments that comprise a repetitive element insertion region;
   (d) comparing repetitive element insertion regions identified in the PBMC sample to the repetitive element insertion regions identified in the tumor sample and/or the cell free nucleic acids sample;
   (e) selecting repetitive element insertion regions that are present in the tumor, but not PBMCs; and
   (g) performing an amplification reaction on cell-free circulating DNA from a serum or plasma sample obtained from the patient after a therapy to determine the level of at least one repetitive element insertion regions selected in (e).

2. The method of claim 1, wherein the repetitive element is an Alu element.

3. The method of claim 1, wherein the repetitive element is a LINE element.

4. The method of claim 1, wherein step (d) further comprises comparing repetitive element insertion regions identified in the PBMC sample to the corresponding regions in the human genome database to identify insertion regions in the PBMC sample that are not present in the human genome database.

5. The method of claim 1, further comprising the steps of adding adapter sequences comprising universal priming sites to each of the DNA fragments and amplifying the DNA fragments, prior to step (c).

6. The method of claim 5, wherein the step of amplifying is carried out using a primer specific to the repetitive element and a universal primer.

7. The method of claim 5, wherein the step of amplifying is carried out using two universal primers.

8. The method of claim 1, further comprising the step of enriching the DNA fragments in at least one of the libraries for DNA fragments that comprise a repetitive element insertion region.

9. The method of claim 8, wherein the step of enrichment is carried out using oligonucleotide probes that specifically hybridize to the repetitive element.

10. The method of any one of the preceding claims, further comprising the step of obtaining a nucleic acid sample from the patient from cell-free nucleic acids post-therapy, which nucleic acids are obtained following the therapy.

11. The method of claim 10, further comprising the step of comparing the repetitive element regions identified the pre-therapy cell-free nucleic acid sample to the post-therapy cell-free nucleic acid sample to identify repetitive element insertion regions that are not detected in the post-therapy cell-free nucleic acid sample.

12. The method of claim 1, wherein the therapy is surgery.

13. The method of claim 1, wherein the patient has a breast tumor.

14. A method of identifying a repetitive element insertion region of a tumor for a patient having the tumor who is to undergo a treatment for the tumor, the method comprising:
   (a) obtaining nucleic acid samples comprising DNA from the patient from each of the following sources: peripheral blood mononuclear cells (PBMCs), the tumor, pre-therapy cell-free nucleic acids, which nucleic acids are obtained prior to a therapy, and cell-free nucleic acids post-therapy, which nucleic acids are obtained following the therapy;
   (b) performing at least one amplification reaction on DNA from each of the nucleic acid samples using a primer to an Alu sequence and a universal primer;
   (c) sequencing in sequencing reactions the DNA obtained from the amplification reactions to determine regions that comprise an Alu insertion sequence relative to the corresponding regions in the human genome database;
   (d) comparing Alu insertion regions identified in step (c) from the PBMC sample to the Alu insertion regions identified in step (c) from the tumor sample to identify Alu insertion regions that are present in the tumor, but not PBMCs;
   (e) comparing the Alu insertion regions identified in step (d) to the Alu insertion regions identified in the cell-free nucleic acid sample from the patient pre-therapy to identify Alu insertion regions that are present in the tumor sample and in the pre-therapy cell-free nucleic acid sample;
   (f) comparing the Alu insertion regions identified in step (e) to the Alu insertion regions identified in the cell-free nucleic acid sample from the patient post-therapy to identify Alu insertion regions that are not detected in the cell-free nucleic acid sample post-therapy; and
   (g) performing an amplification reaction on cell-free circulating DNA from a serum or plasma sample obtained from the patient after the treatment to determine the level of at least one repetitive element insertion regions identified in (f).

15. The method of claim 14, further comprising performing an additional amplification reaction on DNA from each of the nucleic acid samples wherein the second amplification reactions comprising a second primer to an Alu sequence and a second universal primer.

16. The method of claim 15, wherein one of the amplification reactions comprises a primer pair comprising SEQ ID NO:5 and a universal primer.

17. The method of claim 15, wherein one of the amplification reactions comprises a primer pair comprising SEQ ID NO:6 and a universal primer.

18. The method of claim 15, wherein one of the amplification reactions comprises a primer pair comprising SEQ ID NO:5 and a universal primer and the additional amplification reactions comprises a primer pair comprising SEQ ID NO:6 and a universal primer.

19. A method of identifying a repetitive element insertion region of a tumor for a patient having the tumor and who is treated with a therapy to treat the tumor, the method comprising:
   (a) obtaining a nucleic acid sample comprising DNA from circulating nucleic acids pre-therapy and a nucleic acid sample comprising DNA from the circulating nucleic acids post-therapy;
   (b) performing at least one amplification reaction on DNA from each of the nucleic acid samples using a primer to an Alu sequence and a universal primer;
   (c) sequencing in sequencing reactions the DNA obtained from the amplification reactions to determine regions that comprise an Alu insertion sequence relative to a normal human genome and can be uniquely positioned to a defined region in a normal human genome;
   (d) quantifying the level of an Alu insertion region identified in step (c) from the pre-therapy circulating DNA sample in comparison to the level of the Alu insertion regions present in normal controls to identify Alu insertions regions that are present in circulating cell-free DNA at higher levels than normal controls; and
   (e) comparing the level of the Alu insertion regions identified in step (d) to the level of the Alu insertion regions in the post-therapy cell-free DNA sample to identify Alu insertion regions that are not detected at a level different from normal.

* * * * *

SEQUENCE LISTING

<160> NUMBER OF SEQ ID NOS: 33

<210> SEQ ID NO 1
<211> LENGTH: 58
<212> TYPE: DNA
<213> ORGANISM: Artificial Sequence
<220> FEATURE:
<223> OTHER INFORMATION: synthetic P9 adapter oligonucleotide, P9 oligo
<220> FEATURE:
<221> NAME/KEY: modified_base
<222> LOCATION: (1)..(1)
<223> OTHER INFORMATION: g modified by 5' phosphate group

<400> SEQUENCE: 1
gatcggaaga gcatcgcaag gcaagcaagc taaaactgaa ccgggttcct cattagcg        58

<210> SEQ ID NO 2
<211> LENGTH: 58
<212> TYPE: DNA
<213> ORGANISM: Artificial Sequence
<220> FEATURE:
<223> OTHER INFORMATION: synthetic P5 adapter oligonucleotide, P5 oligo
<220> FEATURE:
<221> NAME/KEY: modified_base
<222> LOCATION: (57)..(58)
<223> OTHER INFORMATION: phosphorothioate internucleotide linkage

<400> SEQUENCE: 2
aatgatacgg cgaccaccga gatctacact ctttccctac acgacgctct tccgatct        58

<210> SEQ ID NO 3
<211> LENGTH: 58
<212> TYPE: DNA
<213> ORGANISM: Artificial Sequence

```
<220> FEATURE:
<223> OTHER INFORMATION: synthetic PCR amplification primer
      P9-PCR-Primer

<400> SEQUENCE: 3
cgctaatgag aacccggtt cagttttagc ttgcttgcct tgcgatgctc ttccgatc          58

<210> SEQ ID NO 4
<211> LENGTH: 58
<212> TYPE: DNA
<213> ORGANISM: Artificial Sequence
<220> FEATURE:
<223> OTHER INFORMATION: synthetic PCR amplification primer
      P5-Universal, Alu-enrichment PCR primer P5-Universal

<400> SEQUENCE: 4
aatgatacgg cgaccaccga gatctacact ctttccctac acgacgctct tccgatct          58

<210> SEQ ID NO 5
<211> LENGTH: 56
<212> TYPE: DNA
<213> ORGANISM: Artificial Sequence
<220> FEATURE:
<223> OTHER INFORMATION: synthetic Alu-enrichment PCR primer Alu40.REV

<400> SEQUENCE: 5
gtgactggag ttcagacgtg tgctcttccg atctcccaaa gtgctgggat tacagg          56

<210> SEQ ID NO 6
<211> LENGTH: 58
<212> TYPE: DNA
<213> ORGANISM: Artificial Sequence
<220> FEATURE:
<223> OTHER INFORMATION: synthetic Alu-enrichment PCR primer Alu259.FOR

<400> SEQUENCE: 6
gtgactggag ttcagacgtg tgctcttccg atcggcraca gagcgaracy cygtctca          58

<210> SEQ ID NO 7
<211> LENGTH: 64
<212> TYPE: DNA
<213> ORGANISM: Artificial Sequence
<220> FEATURE:
<223> OTHER INFORMATION: synthetic index-primer, fusion primer with 7 bp
      index sequence
<220> FEATURE:
<221> NAME/KEY: modified_base
<222> LOCATION: (25)..(31)
<223> OTHER INFORMATION: n = g, a, c or t, 7 bp index sequence,
      molecular barcode
<220> FEATURE:
<221> NAME/KEY: misc_feature
<222> LOCATION: (25)..(31)
<223> OTHER INFORMATION: n is a, c, g, or t

<400> SEQUENCE: 7
caagcagaag acggcatacg agatnnnnnn ngtgactgga gttcagacgt gtgctcttcc          60
gatc                                                                      64

<210> SEQ ID NO 8

<400> SEQUENCE: 8

000

<210> SEQ ID NO 9
<211> LENGTH: 60
```

```
<212> TYPE: DNA
<213> ORGANISM: Artificial Sequence
<220> FEATURE:
<223> OTHER INFORMATION: synthetic biotinylated L1-specific
      oligonucleotide probe Probe4000

<400> SEQUENCE: 9
ctggcacaag acagggatgc cctctctcac cgctcctatt caacatagtg ttggaagttc    60

<210> SEQ ID NO 10
<211> LENGTH: 60
<212> TYPE: DNA
<213> ORGANISM: Artificial Sequence
<220> FEATURE:
<223> OTHER INFORMATION: synthetic biotinylated L1-specific
      oligonucleotide probe Probe4117

<400> SEQUENCE: 10
ccccatcgtc tcagcccaaa atctccttaa gctgataagc aacttcagca aagtctcagg    60

<210> SEQ ID NO 11
<211> LENGTH: 60
<212> TYPE: DNA
<213> ORGANISM: Artificial Sequence
<220> FEATURE:
<223> OTHER INFORMATION: synthetic biotinylated L1-specific
      oligonucleotide probe Probe4500

<400> SEQUENCE: 11
ctggaggcat cacactacct gacttcaaac tatactacaa ggctacagta accaaaacag    60

<210> SEQ ID NO 12
<211> LENGTH: 60
<212> TYPE: DNA
<213> ORGANISM: Artificial Sequence
<220> FEATURE:
<223> OTHER INFORMATION: synthetic biotinylated L1-specific
      oligonucleotide probe Probe4759

<400> SEQUENCE: 12
gcaatgggga aaggattccc tatttaataa atggtgctgg gaaaactggc tagccatatg    60

<210> SEQ ID NO 13
<211> LENGTH: 60
<212> TYPE: DNA
<213> ORGANISM: Artificial Sequence
<220> FEATURE:
<223> OTHER INFORMATION: synthetic biotinylated L1-specific
      oligonucleotide probe Probe5000

<400> SEQUENCE: 13
ggcgtgggca aggacttcat gtccaaaaca ccaaaagcaa tggcaacaaa agccaaaatt    60

<210> SEQ ID NO 14
<211> LENGTH: 60
<212> TYPE: DNA
<213> ORGANISM: Artificial Sequence
<220> FEATURE:
<223> OTHER INFORMATION: synthetic biotinylated L1-specific
      oligonucleotide probe Probe5182

<400> SEQUENCE: 14
aaacaacccc atcaaaaagt gggcgaagga catgaacaga cacttctcaa aagaagacat    60

<210> SEQ ID NO 15
<211> LENGTH: 60
<212> TYPE: DNA
```

```
<213> ORGANISM: Artificial Sequence
<220> FEATURE:
<223> OTHER INFORMATION: synthetic biotinylated L1-specific
      oligonucleotide probe Probe5500

<400> SEQUENCE: 15
cactgttggt gggactgtaa actagttcaa ccattgtgga agtcagtgtg gcgattcctc     60

<210> SEQ ID NO 16
<211> LENGTH: 61
<212> TYPE: DNA
<213> ORGANISM: Artificial Sequence
<220> FEATURE:
<223> OTHER INFORMATION: synthetic biotinylated L1-specific
      oligonucleotide probe Probe5699

<400> SEQUENCE: 16
gatgagttca tatcctttgt agggacatgg atgaaattgg aaaccatcat tctcagtaaa     60
c                                                                    61

<210> SEQ ID NO 17
<211> LENGTH: 60
<212> TYPE: DNA
<213> ORGANISM: Artificial Sequence
<220> FEATURE:
<223> OTHER INFORMATION: synthetic biotinylated L1-specific
      oligonucleotide probe Probe6000

<400> SEQUENCE: 17
gggtgcagcg caccagcatg gcacatgtat acatatgtaa ctaacctgca caatgtgcac     60

<210> SEQ ID NO 18
<211> LENGTH: 26
<212> TYPE: DNA
<213> ORGANISM: Artificial Sequence
<220> FEATURE:
<223> OTHER INFORMATION: synthetic PCR primer
      16-chr17:27923338-27923393.F

<400> SEQUENCE: 18
ttgtattact tcttgaccac attaaa                                          26

<210> SEQ ID NO 19
<211> LENGTH: 20
<212> TYPE: DNA
<213> ORGANISM: Artificial Sequence
<220> FEATURE:
<223> OTHER INFORMATION: synthetic PCR primer
      16-chr17:27923338-27923393.R

<400> SEQUENCE: 19 cgaggggag taaaagtgct                                                  20

<210> SEQ ID NO 20
<211> LENGTH: 20
<212> TYPE: DNA
<213> ORGANISM: Artificial Sequence
<220> FEATURE:
<223> OTHER INFORMATION: synthetic PCR primer
      16-chr14:38578285-38578387.F

<400> SEQUENCE: 20
aaatgcacct cttctctcca                                                 20

<210> SEQ ID NO 21
<211> LENGTH: 20
```

```
<212> TYPE: DNA
<213> ORGANISM: Artificial Sequence
<220> FEATURE:
<223> OTHER INFORMATION: synthetic PCR primer
      16-chr14:38578285-38578387.R

<400> SEQUENCE: 21
atgctgagtt ttggactcaa                                              20

<210> SEQ ID NO 22
<211> LENGTH: 21
<212> TYPE: DNA
<213> ORGANISM: Artificial Sequence
<220> FEATURE:
<223> OTHER INFORMATION: synthetic PCR primer
      16-chr3:74888046-74888097.F

<400> SEQUENCE: 22
aaacatcttt aatccccagc a                                            21

<210> SEQ ID NO 23
<211> LENGTH: 23
<212> TYPE: DNA
<213> ORGANISM: Artificial Sequence
<220> FEATURE:
<223> OTHER INFORMATION: synthetic PCR primer
      16-chr3:74888046-74888097.R

<400> SEQUENCE: 23
ttccttagat caggcacatt ttt                                          23

<210> SEQ ID NO 24
<211> LENGTH: 20
<212> TYPE: DNA
<213> ORGANISM: Artificial Sequence
<220> FEATURE:
<223> OTHER INFORMATION: synthetic PCR primer
      5-chr2:159718375-159718655.F

<400> SEQUENCE: 24
gccacaggtc tttgaagagg                                              20

<210> SEQ ID NO 25
<211> LENGTH: 20
<212> TYPE: DNA
<213> ORGANISM: Artificial Sequence
<220> FEATURE:
<223> OTHER INFORMATION: synthetic PCR primer
      5-chr2:159718375-159718655.R

<400> SEQUENCE: 25
ggaacctgca caccctgtat                                              20

<210> SEQ ID NO 26
<211> LENGTH: 26
<212> TYPE: DNA
<213> ORGANISM: Artificial Sequence
<220> FEATURE:
<223> OTHER INFORMATION: synthetic PCR primer
      10-chr13:90100261-90100403.F

<400> SEQUENCE: 26
caaatctcaa gagtttatga tgtacc                                       26

<210> SEQ ID NO 27
<211> LENGTH: 21
<212> TYPE: DNA
```

<213> ORGANISM: Artificial Sequence
<220> FEATURE:
<223> OTHER INFORMATION: synthetic PCR primer
      10-chr13:90100261-90100403.R

<400> SEQUENCE: 27
cctagagaga ttgggggcta a                                        21

<210> SEQ ID NO 28
<211> LENGTH: 22
<212> TYPE: DNA
<213> ORGANISM: Artificial Sequence
<220> FEATURE:
<223> OTHER INFORMATION: synthetic PCR primer
      10-chr2:196460079-196460192.F

<400> SEQUENCE: 28
gcacatttta aaaagcttgc ag                                       22

<210> SEQ ID NO 29
<211> LENGTH: 24
<212> TYPE: DNA
<213> ORGANISM: Artificial Sequence
<220> FEATURE:
<223> OTHER INFORMATION: synthetic PCR primer
      10-chr2:196460079-196460192.R

<400> SEQUENCE: 29
cgaattttct atgtaactga aaca                                     24

<210> SEQ ID NO 30
<211> LENGTH: 21
<212> TYPE: DNA
<213> ORGANISM: Artificial Sequence
<220> FEATURE:
<223> OTHER INFORMATION: synthetic PCR primer
      10-chr10:131942955-131943134.F

<400> SEQUENCE: 30
gagagggctt cctgagatac c                                        21

<210> SEQ ID NO 31
<211> LENGTH: 20
<212> TYPE: DNA
<213> ORGANISM: Artificial Sequence
<220> FEATURE:
<223> OTHER INFORMATION: synthetic PCR primer
      10-chr10:131942955-131943134.R

<400> SEQUENCE: 31
tccaccatcg gagaataagg                                          20

<210> SEQ ID NO 32
<211> LENGTH: 19
<212> TYPE: DNA
<213> ORGANISM: Artificial Sequence
<220> FEATURE:
<223> OTHER INFORMATION: synthetic PCR primer
      12-chr22:33566363-33566494.F

<400> SEQUENCE: 32
agccacatga ccgccttct                                           19

<210> SEQ ID NO 33
<211> LENGTH: 20
<212> TYPE: DNA
<213> ORGANISM: Artificial Sequence

```
<220> FEATURE:
<223> OTHER INFORMATION: synthetic PCR primer
      12-chr22:33566363-33566494.R

<400> SEQUENCE: 33
tgtttgacca ggaccctgac                                              20
```